US006741734B2

United States Patent
Sasaki et al.

(10) Patent No.: US 6,741,734 B2
(45) Date of Patent: May 25, 2004

(54) APPEARANCE INSPECTION METHOD AND APPEARANCE INSPECTION APPARATUS HAVING HIGH INSPECTION PROCESSING SPEED

(75) Inventors: Yoshihiro Sasaki, Tokyo (JP); Masahiko Nagao, Tokyo (JP)

(73) Assignee: NEC Corporation, Tokyo (JP)

( * ) Notice: Subject to any disclaimer, the term of this patent is extended or adjusted under 35 U.S.C. 154(b) by 594 days.

(21) Appl. No.: 09/825,947

(22) Filed: Apr. 5, 2001

(65) Prior Publication Data

US 2001/0028733 A1 Oct. 11, 2001

(30) Foreign Application Priority Data

Apr. 6, 2000 (JP) ........................... 2000-105369

(51) Int. Cl.[7] ................................ G06K 9/00
(52) U.S. Cl. ................ 382/149; 250/559.45; 382/274
(58) Field of Search ................... 382/149, 141–148, 382/150–152, 181, 274, 172, 168; 250/559.4, 559.45; 356/73; 438/16, 15

(56) References Cited

U.S. PATENT DOCUMENTS

| | | | | |
|---|---|---|---|---|
| 4,972,493 A | * | 11/1990 | Chemaly | 382/149 |
| 4,975,972 A | * | 12/1990 | Bose et al. | 382/149 |
| 5,146,510 A | * | 9/1992 | Cox et al. | 382/143 |
| 5,379,347 A | * | 1/1995 | Kato et al. | 382/141 |
| 5,537,669 A | * | 7/1996 | Evans et al. | 382/141 |
| 5,638,460 A | * | 6/1997 | Nishimori et al. | 382/141 |
| 5,640,200 A | * | 6/1997 | Michael | 348/87 |
| 5,720,928 A | * | 2/1998 | Schwartz | 422/186 |
| 5,784,500 A | | 7/1998 | Homma et al. | |
| 5,970,166 A | * | 10/1999 | Nichani | 382/141 |
| 6,005,966 A | * | 12/1999 | Scaman | 382/149 |
| 6,263,292 B1 | * | 7/2001 | Fiekowsky | 702/95 |
| 6,397,165 B1 | * | 5/2002 | Fiekowsky | 702/157 |

FOREIGN PATENT DOCUMENTS

| | | |
|---|---|---|
| EP | 0 341 685 B1 | 9/1995 |
| JP | 05-264240 | 10/1993 |
| JP | 07-37094 | 2/1995 |
| JP | 07-128249 | 5/1995 |
| JP | 07-229842 | 8/1995 |
| JP | 08-14845 | 1/1996 |
| JP | 08-44870 | 2/1996 |
| JP | 09-015165 A | 1/1997 |
| JP | 09-033342 A | 2/1997 |
| JP | 10-143653 A | 5/1998 |
| JP | 10-213417 | 8/1998 |
| JP | 11-14317 | 1/1999 |
| JP | 11-017317 A | 1/1999 |
| JP | 11-63951 | 3/1999 |
| JP | 11-135054 | 5/1999 |
| JP | 11-259434 | 9/1999 |
| JP | 2000-132687 A | 5/2000 |
| JP | 2001-184510 A | 7/2001 |

* cited by examiner

Primary Examiner—Jayanti K. Patel
(74) Attorney, Agent, or Firm—Sughrue Mion, PLLC

(57) ABSTRACT

An appearance inspection method, includes (a), (b), (c), (d), (e), (f), (g), and (h). The (a) includes providing an image data in which an inspected sample is photographed. The (b) includes detecting a brightness of each of a plurality of image units included in the image data based on the image data. The (c) includes detecting the number of the image units being identical with each other in the brightness for each of the brightness. The (d) includes detecting, as a measured maximum number, the number that is maximum of the detected numbers as a result of the (c). The (e) includes computing the measured maximum number to determine a set maximum number. The (f) includes determining a threshold level of the brightness based on the set maximum number. The (g) includes converting the image data into a binary pattern based on the threshold level. The (h) includes detecting a defect of the inspected sample based on the binary pattern.

21 Claims, 14 Drawing Sheets

EXPANDING/CONTRACTING PROCESS

CONTRACTING/EXPANDING PROCESS

APPEARANCE INSPECTION METHOD AND APPEARANCE INSPECTION APPARATUS HAVING HIGH INSPECTION PROCESSING SPEED

BACKGROUND OF THE INVENTION

1. Field of the Invention

The present invention relates to an appearance inspection method and an appearance inspection apparatus. More particularly, the present invention relates to an appearance inspection method and an appearance inspection apparatus for an IC package.

2. Description of the Related Art

Conventionally, the following techniques have been well known as an appearance inspection apparatus for an IC package.

Japanese Laid Open Patent Application (JP-A-Heisei, 10-213417) discloses the following method of detecting a position of an IC package. A boundary between a side surface and a top surface of a package is detected by using a histogram. The linearity of a continuous distribution of respective dots is detected from the differential values of distributions at boundary points. Also, a package boundary straight line is detected by using a least square method, from the remaining dots in which non-linear sections caused by loss are removed. Moreover, an intersection of the detected straight lines in an x-direction and a y-direction is assumed to be an origin. Then, the x, y straight lines are rotated by angles equal to each other so that an angle between the two straight lines with the origin as a center is 90 degrees. Then, an x-direction standard axis and a y-direction standard axis are calculated. Accordingly, even if there are a loss, a burr and the like, it is possible to correctly detect the IC position and also possible to correctly set a detection position of a defect item with regard to an appearance inspection, a detection position of a lead and the like.

Japanese Laid Open Patent Application (JP-A-Heisei, 11-14317) discloses the following appearance inspection method. An IC package is photographed by using a TV camera. With regard to a picture data, a scanning start area is set on the periphery of the IC package by using an area set device of a picture data processor, and the scanning is done. A position data group at an end of the IC package is detected by a position data detector. In accordance with this position data group, an inspection target region is set for the picture data by using an inspection target region set device. A picture process is done by a judging device. Then, it is judged whether the IC package is allowed or rejected.

Japanese Laid Open Patent Application (JP-A-Heisei, 7-128249) discloses the following IC extraneous substance detector. A camera photographs a lead of an inspection target IC. An AD converter carries out an AD-conversion. A differential circuit receives a light/shade picture data, and carries out a differential process so that a change point of a concentration is highlighted, and then outputs a differential picture data. A first binary circuit converts a differential picture data in an inspection target region including a plurality of leads stored in an inspection region store circuit into a binary picture data, in accordance with a preset first binary level, and outputs it. A projection circuit measures the number of "1" of the binary picture data in a direction parallel to a longitudinal direction of the lead, and outputs the measured data, and carries out a binary process, and then measures the number of "1" of the binary data in the longitudinal direction of the lead. A second binary circuit converts the measured data into a binary value. A judging circuit counts the continuous number of "0" and "1" in a second binary data, and judges as a deposition of the extraneous substance if there is the continuous numeral without a preset range between an upper limit value and a lower limit value.

Japanese Laid Open Patent Application (JP-A-Heisei, 7-37094) discloses the following picture processor. This is provided with: an editor for editing a history of a picture process program stored in a history program memory; and a corrector for deleting a duplex portion in a picture process command list and an unnecessary component to obtain a final result. An indication from which a user can understand a picture process command and learn a usage method is displayed on a display. An illumination manner suitable for a target sample is determined from an evaluation value of the result treated by the picture processor. A picture process program is generated in accordance with an evaluation value of a feature amount. Also, a function is displayed after a selection based on a combination of measurement values. Then, a function selected on the basis of the indication is added to the picture process program.

Japanese Laid Open Patent Application (JP-A-Heisei, 8-44870) discloses the following method for managing a memory of an appearance inspection apparatus. A non-volatile memory can register therein an environment data with regard to a usage condition, a kind data set for each inspected sample and a user program. The store region of the non-volatile memory is divided into many blocks of a certain size. Also, the non-volatile memory has an allocation table indicative of a correspondence relation between a content stored in each block and a stored block.

Japanese Laid Open Patent Application (JP-A-Heisel, 5-264240) discloses the following appearance inspection apparatus. This is provided with: a photographing device for photographing a pattern formed on a sample; a picture binary converter for converting a photographed picture into a binary value; a radial length measuring device for measuring a length of a pattern in a pattern portion within each of pixel rows extending in a plurality of directions from any central pixel on a binary picture; a center detector for detecting a substantial center of a pattern from the measured lengths in the plurality of directions; a coding device for converting each of the measured lengths in the plurality of directions into a radial code; and a category converter for storing therein in advance a category code indicative of a kind of a pattern form corresponding to each of the various radial codes, and selecting a category stored in accordance with the radial code converted by the coding device, and then converting into the category code. Accordingly, it detects a defect of a pattern in accordance with the category code.

Japanese Laid Open Patent Application (JP-A-Heisei, 7-229842) discloses the following apparatus for inspecting an extraneous substance of IC. This apparatus for inspecting an extraneous substance of IC is provided with: a camera for photographing an IC composed of a shoulder where a lead targeted for an inspection is located in a flat portion on a mold side, a plane on a tip side and a slope located in a middle between those portions; an AD converter for receiving a picture data from the camera, carrying out an AD conversion and outputting a light/shade picture data; an inspection region cutter for cutting an inspection region light/shade picture data in a range including all leads corresponding to one side of the IC from the light/shade picture data; a first binary converter for converting the inspection region light/shade picture data into a binary value so that only the shoulder and the plane of the lead, in which a reflection light amount received by the camera is large, become at "1"; a projecting device for receiving the binary picture data converted into the binary value by the first binary converter, and outputting an X projection data in which the number of "1" pixels in each picture pixel row in an X-direction vertical to a longitudinal direction of the lead is measured; a lead region divider for defining as a slant picture the portion corresponding to a center of the lead in a section where the X projection data in the inspection region light/shade picture data is smaller than a predetermined value, defining as a shoulder picture the portion corresponding to a portion on a mold side of the IC and having a value greater than the predetermined value, and defining as a plane picture the portion corresponding to a portion on the tip of the lead and having a value greater than the predetermined value; and a device for detecting an extraneous substance for each division region, which converts each of the shoulder picture, the slant picture and the plane picture into a binary value in accordance with a binary level peculiar to each of the pictures, identifies the "1" pixel as the portion of the lead, and then detects the extraneous substance deposited on the lead.

Japanese Laid Open Patent Application (JP-A-Heisei, 8-14845) discloses the following apparatus for inspecting an extraneous substance of an IC. The apparatus for inspecting an extraneous substance of an IC is provided with: a photographing device for photographing an IC targeted for an inspection and outputting an analog picture data; an AD converter for receiving the analog picture data, carrying out an AD conversion and outputting as a light/shade picture data; an inspection region cutter for receiving the light/shade picture data and cutting the light/shade picture data in a portion including all leads corresponding to one side of the IC, in a predetermined range; a memory for storing therein the cut light/shade picture data in the inspection region; a first binary converter for receiving the light/shade picture data from the memory, and converting into a binary value in accordance with a predetermined high binary level in which only a lead where an incident light amount to the photographing device is maximum is set to "1", and a portion where the incident light amount is smaller than that of the lead is set at "0"; a first projector for receiving the binary light/shade picture data outputted by the first binary converter, and counting the number of "1" in a Y-direction parallel to a longitudinal direction of the lead for each position in an X-direction vertical to the longitudinal direction of the lead; a second binary converter for receiving a first projection data outputted by the first projector, and converting into a binary value in accordance with the preset high binary level in order to detect the extraneous substance on the lead; a differential device for receiving the light/shade picture data from the memory, carrying out a differential process, and outputting as a differential light/shade picture data; a third binary converter for receiving the differential light/shade picture data, and converting into a binary value in accordance with a predetermined low binary level in which only a portion between the leads where the incident light amount to the photographing device is minimum is set to "0", and a portion where the incident light amount is larger than that of the portion between the leads is set at "1", a second projector for receiving the binary differential light/shade picture data outputted by the third binary converter, and counting the number of "1" in the Y-direction for each position in the X-direction; a fourth binary converter for receiving a second projection data outputted by the second projector, and converting into a binary value in accordance with the predetermined low binary level in order to detect an extraneous substance between the leads; a detection region cutter for retrieving "1" in the first binary projection data outputted by the second binary converter and "0" in the second binary projection data outputted by the fourth binary converter, with regard to the X-direction, and determining the positions of the two "0" firstly located in respective outer directions with respect to the two "1" located at both ends, and then specifying the section between the positions of the two "0" as an extraneous substance detection target range; a lead extraneous substance detector for counting the continuous number of "1" and the continuous number of "0" in the first binary projection data, within the extraneous substance detection target range specified by the detection region cutter, and then judging whether or not the extraneous substance exists on the lead, in accordance with the fact whether or not they are within the predetermined ranges; and a lead-to-lead extraneous substance detector for counting the continuous number of "1" and the continuous number of "0" in the second binary projection data, within the extraneous substance detection target range specified by the detection region cutter, and then judging whether or not the extraneous substance exists between the leads, in accordance with the fact whether or not they are within the predetermined ranges.

Japanese Laid Open Patent Application (JP-A-Heisei, 11-63951) discloses the following appearance inspection apparatus. This appearance inspection apparatus is the apparatus for inspecting the appearance of a package, such as a BGA CSP type IC and the like, in which a mark is affixed on a top surface, and a terminal for electric connection is formed on a rear surface. It is provided with: a pickup for picking up the package accommodated in a tray in a manner that a terminal surface is facing downward, and then sending to a measurement position; a mark package void inspector mounted above a pickup position of the package from the tray; and a measuring device for inspecting a terminal side of the packaged sent to the measurement position in the condition that the top portion is held by the pickup, by using a picture process measurement or a laser deviation measurement. The package void inspector inspects a next package located at a pickup position in a course when the pickup sends the package after the inspection of the mark package void to the measurement position.

Japanese Laid Open Patent Application (JP-A-Heisei, 11-135054) discloses the following charged particle beam device. This charged particle beam device is provided with: a device for irradiating a charged particle beam to a sample; a sample signal detector for detecting a sample signal sent from the sample; an AD converter for converting the detection signal of the sample signal detector into a digital signal; a basic picture processor for processing the digital signal from the AD converter by using a dedicated circuit; a picture memory for storing therein as a picture data the signal processed by the basic picture processor; and a display for displaying thereon the picture data stored in the picture memory. This is further provided with a parallel picture processor including one mask CPU and a plurality of slave CPUs. The picture data stored in the picture memory is sent to the parallel picture processor. The master CPU carries out the control so that the transferred picture data is processed by the plurality of slave CPUs, in parallel, one part at a time.

Japanese Laid Open Patent Application (JP-A-Heisei, 11-259434) discloses the following parallel data processor. This parallel data processor is provided with a data input device which is driven by a drive signal sent through a drive signal bus and receives a digital signal at a predetermined first state of the drive signal; a plurality of processor elements to which the digital signal received by the data input device through a data bus is sent through the data bus; and a process distributor for communicating with the plurality of processor elements through a communication bus, at a second state of the drive signal at which the data input device does not receive the digital signal. The process distributor has a device for monitoring the states of the plurality of processor elements when the drive signal is at the second state, and determining the processor element which distributes and processes the digital signal from the data input device, depending on the monitored result.

An appearance inspection method and an appearance inspection apparatus are desirable which have a higher speed of an inspection process.

In particular, an appearance inspection method and an appearance inspection apparatus are desirable which have a higher speed of an inspection process when a plurality of inspection items are inspected.

An appearance inspection method and an appearance inspection apparatus are desirable which have a high inspection accuracy without any influence from noise component.

An appearance inspection method and an appearance inspection apparatus are desirable which agree with a property of each inspection target region.

An appearance inspection method and an appearance inspection apparatus are desirable which are convenient for a user.

SUMMARY OF THE INVENTION

The present invention is accomplished in view of the above mentioned problems. Therefore, an object of the present invention is to provide an appearance inspection method and an appearance inspection apparatus which have a higher speed of an inspection process. In particular, it is to provide an appearance inspection method and an appearance inspection apparatus which have a higher speed of an inspection process when a plurality of inspection items are inspected. Another object of the present invention is to provide an appearance inspection method and an appearance inspection apparatus which have a high inspection accuracy without any influence from noise component. Still another object of the present invention is to provide an appearance inspection method and an appearance inspection apparatus which agree with a property of each inspection target region. Still another object of the present invention is to provide an appearance inspection method and an appearance inspection apparatus which are convenient for a user.

In order to achieve an aspect of the present invention, an appearance inspection method, includes: (a) providing an image data in which an inspected sample is photographed; (b) detecting a brightness of each of a plurality of image units included in the image data based on the image data; (c) detecting the number of the image units being identical with each other in the brightness for each of the brightness; (d) detecting, as a measured maximum number, the number that is maximum of the detected numbers as a result of the (c); (e) computing the measured maximum number to determine a set maximum number; (f) determining a threshold level of the brightness based on the set maximum number; (g) converting the image data into a binary pattern based on the threshold level; and (h) detecting a defect of the inspected sample based on the binary pattern.

In this case, the set maximum number corresponds to a result when a noise component is removed from the measured maximum number.

Also in this case, the (e) is performed with first and second numbers, the first number corresponding to higher brightness with reference to the brightness corresponding to the measured maximum number, and the second number corresponding to lower brightness with reference to the brightness corresponding to the measured maximum number.

Further in this case, the (e) is performed with the brightness corresponding to the number identical with a subtracted value after subtracting a predetermined value from the measured maximum number.

In this case, a result of the (b) is represented by a histogram, and wherein in the (e), a portion in which the number is larger than a subtracted value after subtracting a predetermined value from the measured maximum number of a waveform of the histogram, is approximated to a quadratic curve, and wherein a peak value of the quadratic curve is detected as the set maximum number.

Also in this case, thr=the set maximum number X a multiplication value+an offset value, and wherein thr is the threshold level of the (f).

Further in this case, at least one of the multiplication value and the offset value is different for each of a plurality of inspection items with regard to the inspected sample.

In this case, the inspected sample is an IC package, and the plurality of inspection items include a void inspection, a detection of a package crack and a package defect, a seal inspection, an extraneous substance on a lead inspection, and an extraneous substance between leads inspection.

Also in this case, when an inspecting target area to detect the defect is smaller than a preset value, the threshold level is not determined at the (d), (e) and (f), and a predetermined standard value is used as the threshold level.

Further in this case, the inspected sample is an IC package, a concave section is formed in the IC package, the concave section being provided for a pin to push the IC package out of a mold making industry when the IC package is molded, and wherein when an inspecting target area to detect the defect is the concave section, the threshold level is not determined at the (d), (e) and (f), and two predetermined standard values are used as the threshold level, and wherein the converting of the (g) is performed two time by using the two predetermined standard values as the threshold level, respectively to produce two the binary patterns, and wherein the (h) includes detecting different kind of the defect with each other based on each of the two binary patterns, respectively.

In this case, the inspected sample is an IC package, and the IC package includes a seal, and wherein when an inspecting target area to detect the defect is the seal, the (b) includes detecting the brightness of a seal inspection portion in which the seal is expected to exist of the image data, and wherein the (c) includes detecting the number of the image units with regard to the seal inspection portion.

Also in this case, the inspected sample is an IC package, and the IC package includes a seal, and wherein a result of the (b) is represented by a histogram, and wherein when an inspecting target area to detect the defect is the seal, the (f) includes scanning a waveform of the histogram from the set maximum number as a beginning point in direction to higher brightness, and wherein the (f) includes detecting a peak value of a first upward convex curve next to a second upward convex curve including the set maximum number of the waveform as a result of the scanning, and wherein thr=(the set maximum number+the peak value)/2, and wherein thr is the threshold level of the (f).

Further in this case, the inspected sample is an IC package, and the IC package includes a seal, and wherein a result of the (b) is represented by a histogram, and wherein when an inspecting target area to detect the defect is the seal, the (f) includes scanning a waveform of the histogram from the set maximum number as a beginning point in direction to higher brightness, and wherein the (f) includes detecting a peak value of a first upward convex curve next to a downward concave portion of a second upward convex curve including the set maximum number of the waveform as a result of the scanning, and wherein thr=(the set maximum number+the peak value)/2, and wherein thr is the threshold level of the (f).

In this case, the inspected sample is an IC package, and the IC package includes a seal, and wherein a result of the (b) is represented by a histogram, and wherein when an inspecting target area to detect the defect is the seal, the (f) includes setting a range corresponding to a predetermined brightness of the histogram as a seal inspection portion, and wherein a peak value in the seal inspection portion of a waveform of the histogram is detected, and wherein thr=(the set maximum number+the peak value)/2, and wherein thr is the threshold level of the (f).

Also in this case, the inspected sample is an IC package, and the IC package includes a seal, and wherein a result of the (b) is represented by a histogram, and wherein when an inspecting target area to detect the defect is the seal, the (f) includes setting a range in which Es is the lowest point in the brightness of the histogram as a seal inspection portion, and wherein the Es=the set maximum number X a set multiplication value+a set offset value, and wherein a peak value in the seal inspection portion of a waveform of the histogram is detected, and wherein thr=(the set maximum number+the peak value)/2, and wherein thr is the threshold level of the (f).

In order to achieve another aspect of the present invention, an appearance inspection apparatus, includes: a camera photographing an inspected sample to produce an image data of the inspected sample; a threshold level providing section providing a threshold level; a binary converting section converting the image data into a binary pattern based on the threshold level; and a judging section judging whether the inspected sample is passed or failed based on the binary pattern, and wherein the threshold level providing section detects a brightness of each of a plurality of image units included in the image data based on the image data, and detects the number of the image units being identical with each other in the brightness for each of the brightness, and detects, as a measured maximum number, the number that is maximum of the detected numbers, and computes the measured maximum number to determine a set maximum number, and provides the threshold level based on the set maximum number.

In order to achieve still another aspect of the present invention, an appearance inspection apparatus, includes: an image processing library storing a plurality of image processing items; an inspection library storing a plurality of inspection item data, in which the plurality of image processing items are selected arbitrarily and in which the selected image processing items are performed in an arbitrary turn, and wherein a binary converting process is included in the plurality of image processing items, and wherein the binary converting process includes detecting a brightness of each of a plurality of image units included in an image data in which an inspected sample is photographed based on the image data, when providing a threshold level used in the binary converting process, and detecting the number of the image units being identical with each other in the brightness for each of the brightness, and detecting, as a measured maximum number, the number that is maximum of the detected numbers, and computing the measured maximum number to determine a set maximum number, and providing the threshold level based on the set maximum number.

In this case, the appearance inspection apparatus further includes: an inspection data for each kind library storing a plurality of inspection data for each kind for an inspection target product, in which the plurality of inspection item data are selected arbitrarily in which the selected inspection item data are performed in an arbitrary turn.

Also in this case, a plurality of the inspection item data includes data for a void inspection, data for a seal inspection, data for a mold loss inspection, data for an IC package direction difference detection and data for a lead curve detection.

Further in this case, a plurality of the inspection item data includes a parameter used in the computation included in the binary converting process.

In order to achieve yet still another aspect of the present invention, a computer readable recording medium for recording a program for a process, includes: (a) providing an image data in which an inspected sample is photographed; (b) detecting a brightness of each of a plurality of image units included in the image data based on the image data; (c) detecting the number of the image units being identical with each other in the brightness for each of the brightness; (d) detecting, as a measured maximum number, the number that is maximum of the detected numbers as a result of the (c); (e) computing the measured maximum number to determine a set maximum number; (f) determining a threshold level of the brightness based on the set maximum number; (g) converting the image data into a binary pattern based on the threshold level; and (h) detecting a defect of the inspected sample based on the binary pattern.

In the present invention, a picture processing algorithm (inspection algorithm) is generated in which various algorithms of pre-registered picture processes are combined and duplicated in any order by a user. The user gives any name to the duplicated picture processing algorithm, and it is registered.

The user specifies the picture processing algorithm generated uniquely as mentioned above, within an inspection data for each kind, by using the name at the time of its registration. Thus, its picture processing algorithm is commonly used even in generating a different kind of inspection data. Moreover, the picture processing algorithm is individually changed in the inspection data for each kind.

In the inspection data for each kind, the picture processing algorithm, an inspection region and a judgment value are set. At a time of an automatic inspection, the picture process is done in a specified inspection region, in accordance with a preset inspection data. A finally measured value is compared with the judgment value. Accordingly, whether it is allowed or rejected is judged.

Its inspection result is outputted to any address for each inspection item arbitrarily generated by the user.

DESCRIPTION OF THE PREFERRED EMBODIMENTS

An embodiment of an appearance inspection method according to the present invention will be described below with reference to the attached drawings.

An appearance inspection method of an IC package in a first embodiment has the steps of: detecting a position of the IC package; generating a histogram; setting a threshold level; and converting into a binary value.

Figure 1A:
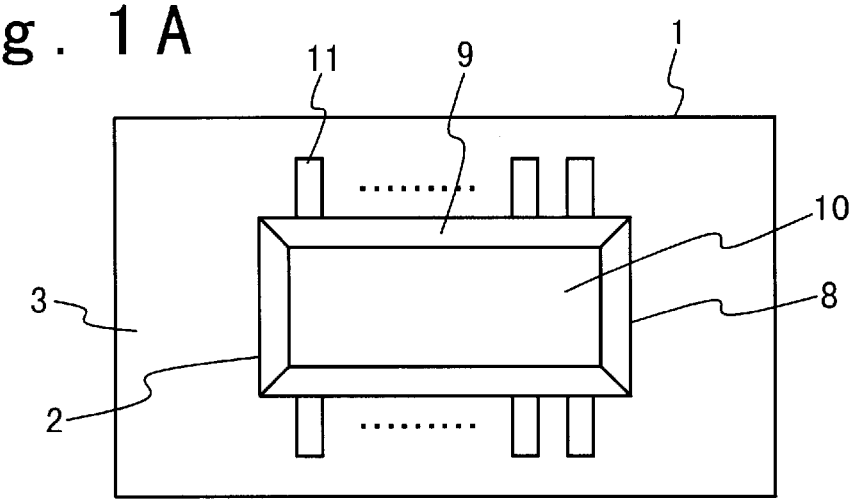
FIG. 1A is a plan view showing a photograph screen of an IC package, in an embodiment of an appearance inspection method according to the present invention.
Figure 1B:
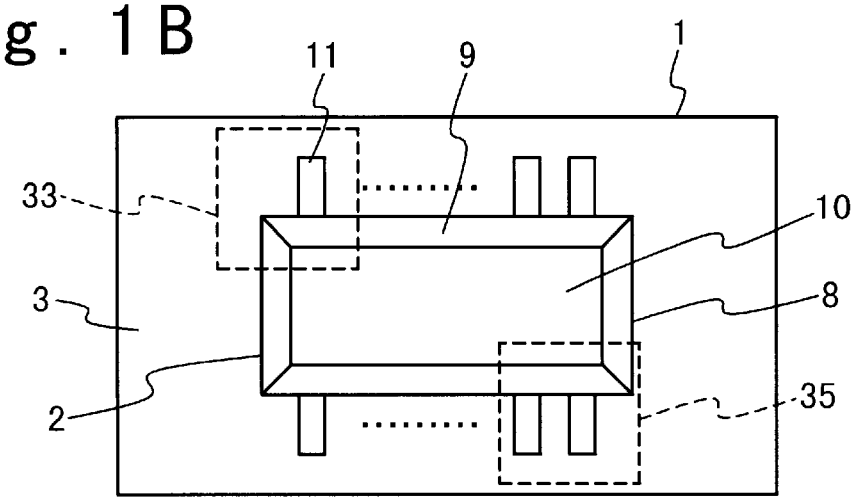
FIG. 1B is a view showing a package corner detection window.
Figure 1C:
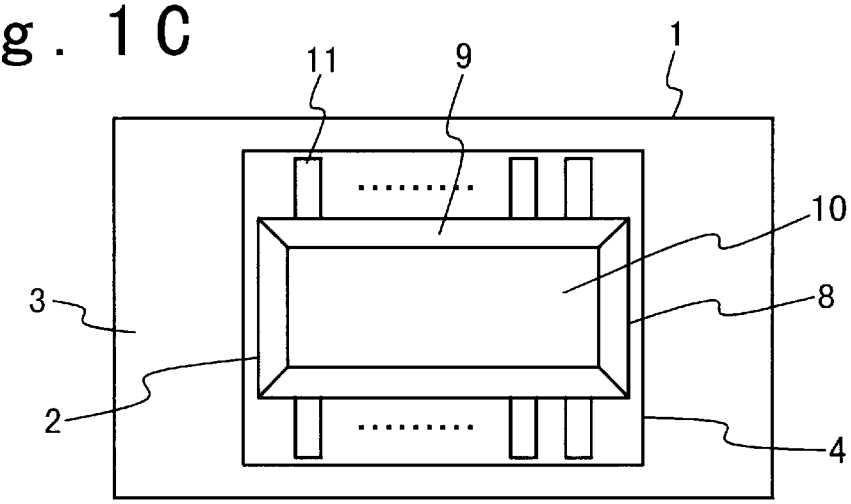
FIG. 1C is a view showing a data treatment range window.

The step of detecting the position of the IC package is described with reference to FIGS. 1A, 1B and 1C. FIG. 1A is a plan view showing a photograph picture of the IC package. FIG. 1B is a view showing a package corner detection window. And, FIG. 1C is a view showing a data treatment range window.

At first, a CCD camera photographs a package of an IC (Integrated Circuit). In FIG. 1A, a symbol 1 denotes the photographed picture. Its picture signal is digitized and stored in a picture memory as an IC package picture data.

An IC picture 2 is mounted at a substantial center of a photograph picture 1. The IC picture 2 includes a top surface 10 of an IC package 8, a side 9 of the IC package 8 and a lead 11 of the IC. A symbol 3 denotes a background picture.

When the IC is photographed, the IC is located at a predetermined position under the CCD camera. As shown in FIG. 1B, an upper left package corner detection window 33 and a low right package corner detection window 35 are set for regions in which an upper left portion of the IC package 8 and a low right portion thereof are expected to be respectively located.

A model picture data at an upper left corner of an IC package serving as a model and a low right corner thereof is stored in advance in a memory. Portions in coincidence with an upper left corner model picture data and a low right corner model picture data are detected by a pattern matching method, within the respective ranges of the upper left package corner detection window 33 and the low right package corner detection window 35. This results in a detection of a position coordinate of an end of the IC package 8. A position of the IC picture 2 is determined in accordance with the detected position coordinate. A data treatment range window 4, which is an inspection target region in the photograph picture 1, is set as shown in FIG. 1C, in accordance with a position of the IC picture 2.

The step of generating a histogram will be described below with reference to FIG. 2.

Figure 2:
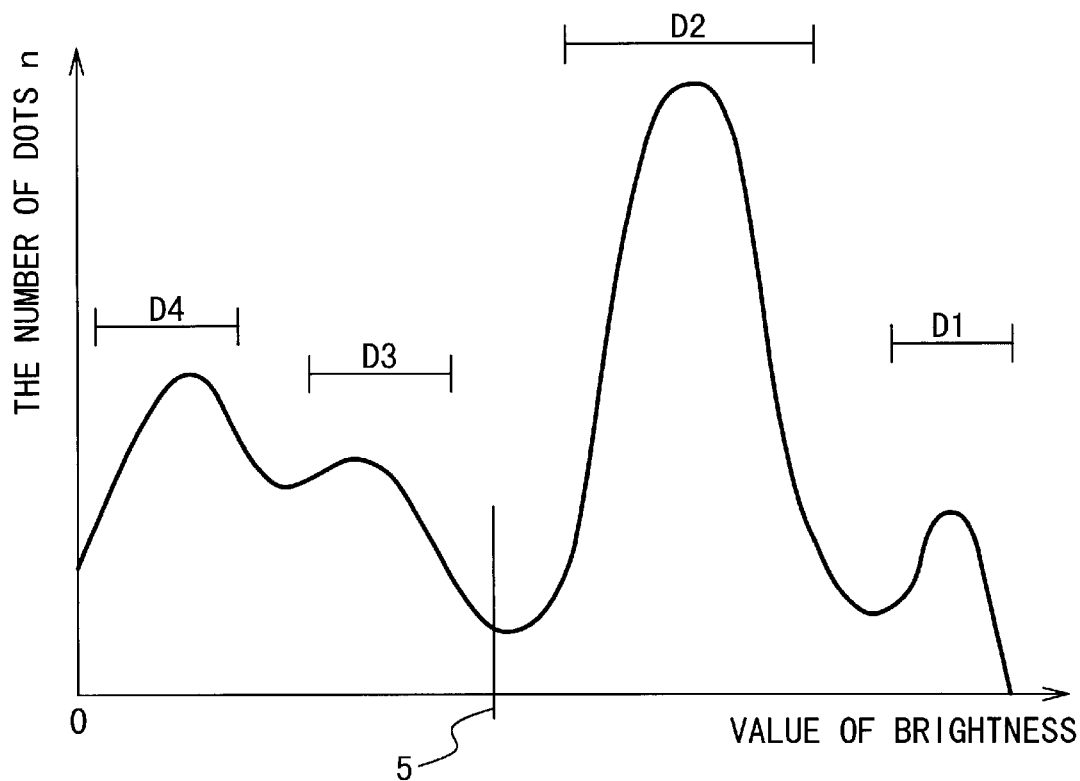
FIG. 2 is a brightness and dot number property view showing a brightness distribution state of a photograph screen.

FIG. 2 is a brightness dot number property view showing the brightness distribution state of the photograph screen 1 in the data treatment range window 4 of FIG. 1C. As shown in FIG. 2, a histogram in which with all dots in the data treatment range window 4 as a target, a horizontal axis indicates a value of a brightness (luminance) and a vertical axis indicates the number of dots is generated. In the photograph picture 1, the respective dots constituting the photograph picture 1 are represented as an 8-bit data, and they are processed as mono-chrome data of 256 gradations. A scale (not shown) of the brightness in FIG. 2 is set between 0 and 255, and it corresponds to the 256 gradations.

In a histogram wave form of FIG. 2, a mountain D1 having the highest brightness indicates the number of dots in the lead 11. A mountain D2 having the next highest brightness indicates the number of dots on the package top surface 10. A mountain D3 having the next highest brightness after the mountain D2 indicates the number of dots on the package side 9. A mountain D4 having the lowest brightness indicates the number of dots in a background picture 3.

The step of setting a threshold level will be described below.

Here, a case is described in which a lower limit value between the mountain D2 having the second highest brightness and the mountain D3 having the third highest brightness is set as a threshold level 5. In this case, a picture on the package top surface 10 and a picture on the package side 9 are cut and separated from each other.

The step of converting into a binary value will be described below.

Figure 3:
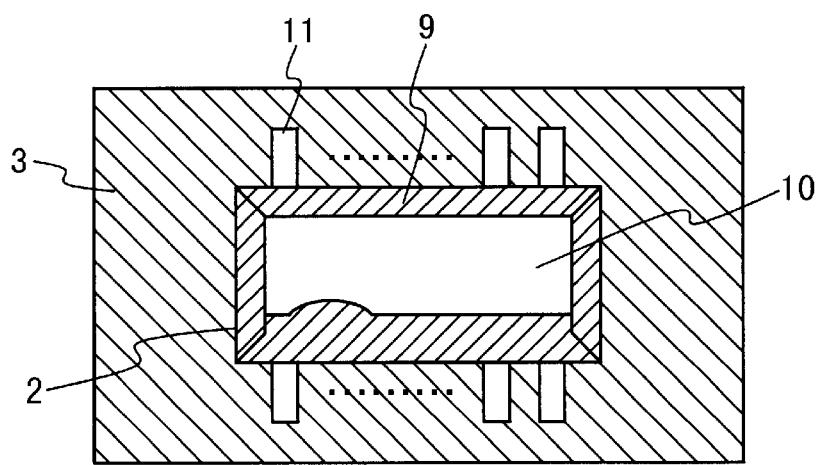
FIG. 3 is a view showing a screen in which a photograph screen of a data treatment range is converted into a binary value, in accordance with a threshold level.

FIG. 3 shows the picture in which the photograph picture 1 in the data treatment range window 4 is converted into a binary value, in accordance with the threshold level 5. The package top surface 10 and the lead 11 having the higher brightness than the threshold level 5 are displayed as white. The background picture 3 and the package side 9 having the lower brightness than the threshold level 5 are displayed as black.

In FIG. 3, the fact that on the lower side of the package, the black picture corresponding to the package side 9 is wider in width than the other sides implies that there is a loss in a boundary between the side 9 and the top surface 10 in the package.

As mentioned above, in accordance with the threshold level (brightness value) obtained from the histogram wave form, the photograph picture is converted into the binary value to thereby detect a defect, such as a loss, a dirt and the like.

In this embodiment, the threshold level is determined by the following method, at the step of setting the threshold level.

<1>Smoothing of Peak Value

A peak value $n'_a$ in which the number of dots is maximum is determined in the histogram wave form shown in FIG. 2. The peak value $n'_a$ is not a value directly read from the histogram wave form, and it is determined as a smoothed result as described below. As denoted by a symbol K of FIG. 4, the histogram wave form is not an actually smoothed curve, and it includes minute concaves and convexes. The smoothing operation is done in order to remove the influence, such as an error and the like, which brings about the minute concaves and convexes.

Figure 4:
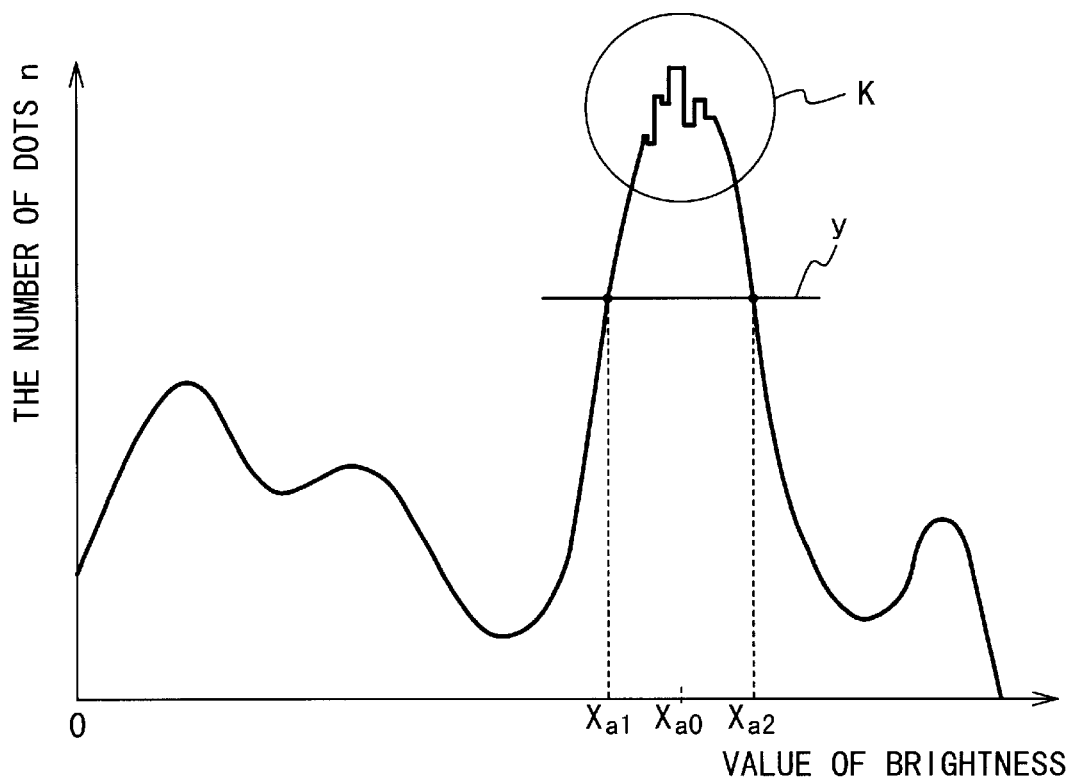
FIG. 4 is a view describing a problem when a peak value is determined from a histogram of FIG. 2.

At first, a numeral $n_a$ (a value directly read from the histogram wave form) actually having the maximum number of dots is detected in the histogram wave form of FIG. 2 (FIG. 4). Then, in FIG. 2, a dot numeral $n_{a-1}$ having a brightness value smaller by an amount corresponding to one scale than a brightness value corresponding to the $n_a$ and a dot numeral $n_{a+1}$ having a brightness value greater by the amount corresponding to one scale than the brightness value corresponding to the $n_a$ are detected.

The smoothed peak value $n'_a$ is determined from the following equation (1):

$$n'_a = (n_{a-1} + n_a + n_{a+1})/3 \qquad (1)$$

In the above-mentioned case, it is smoothed on the basis of the three elements. However, the number of elements is not limited to 3. The number may be arbitrary. If the number of elements is 5, the dot numerals $n_{a-1}$, $n_{a-2}$ having the brightness values smaller by the amounts corresponding to one scale and two scales than the brightness value corresponding to the $n_a$, respectively, and the dot numerals $n_{a+1}$, $n_{a+2}$ having the brightness values greater by the amounts corresponding to one scale and two scales than the brightness value corresponding to the $n_a$, respectively, are determined in FIG. 2.

The $n'_a$ is determined by the following equation (2):

$$n'_a = (n_{a-2} + n_{a-1} + n_a + n_{a+1} + n_{a+2})/5 \qquad (2)$$

Even if the number of elements is another value besides 3 and 5, the $n'_a$ can be determined by the same manner as the above-mentioned case.

<2>Calculation of Threshold Level (Binary Level)

A threshold level thr is determined in accordance with the smoothed peak value $n'_a$ calculated by the equation <1>by using the following equation (3):

$$thr = n'_a \times \text{Multiplication Value} + \text{Offset Value} \qquad (3)$$

In the equation (3), the multiplication value and/or the offset value can be varied so as to follow the change in a photograph condition, such as an illustration condition and the like (so as not to suffer from any influence from its change). Here, the illumination condition implies the illumination strength when the IC package is illuminated when the IC package is photographed.

Moreover, in the equation (3), the multiplication value and/or the offset value can be varied depending on the inspection item.

Here, the inspection item includes the respective items of a detection of a void, a detection of a package crack and loss, an inspection of a seal, a detection of an extraneous substance on a lead and a detection of an extraneous substance between leads. Here, the void implies the fact that the bubble formed when the IC package 8 made of resin is molded appears as a small hole on the IC package 8.

The brightness of the void is lower than that on the top surface 10 of the IC package 8 of the allowed product.

The brightnesses in the package crack, the package loss, the seal, and the extraneous substances on the lead 11 and between the leads are higher than that of the brightness on the top surface 10 of the IC package 8 of the allowed product, and the respective brightnesses are different from each other.

A brightness of a detected defect is different for each inspection item. Thus, it is desirable that the threshold level thr is not singly determined in converting into a binary value for the judgment of the allowance or rejection and it is individually set for each inspection item. Thus, the multiplication value and/or the offset value of the equation (3) can be varied for each inspection item.

When a void having a lower brightness than that on the top surface 10 of the IC package 8 of the allowed product is detected, the thr is set as a brightness lower than the brightness corresponding to the $n'_a$. The void is detected as the component having the brightness lower than that of the thr after the binary conversion process based on the thr.

When a white dust having the higher brightness than that on the top surface 10 of the IC package 8 of the allowed product or the like is detected, the thr is set as a brightness higher than the brightness corresponding to the $n'_a$. The white dust or the like is detected as the component having the brightness higher than that of the thr after the binary conversion process based on the thr.

The smoothed peak value $n'_a$ can be determined by the method using the following equations (4) and (5), instead of the calculation method using the equations (1) and (2):

$$n_a - \text{Set Value} = y \qquad (4)$$

The y determined from the equation (4) is indicated such as a straight line y of FIG. 4.

Let us suppose that the brightnesses corresponding to the two intersections of the histogram wave form and the straight line y are $x_{a1}$, $x_{a2}$, respectively:

$$(x_{a1} + x_{a2})2 = x_{a0} \qquad (5)$$

In FIG. 4, the number of dots corresponding to the brightness $x_{a0}$ determined from the equation (5) is assumed to be the smoothed peak value $n'_a$.

Moreover, the $n'_a$ can be determined by using the following method, instead of the above-mentioned two methods.

In the histogram wave form of FIG. 4, the portion located over the straight line y determined by the equation (4) (the portion of the mountain including the concaves and the convexes) is approximated to a quadratic curve. The value implying a peak on the quadratic curve determined from the approximation is the $n'_a$.

The threshold level thr is determined by any of the above-mentioned methods without any influence from the noise component represented by the concave and the convex in the histogram wave form.

In this embodiment, as shown in the equation (3), the threshold level thr is calculated on the basis of the $n'_a$ implying the peak value of the histogram wave form.

Here, it may be considered to calculate the threshold level thr from the following equation (6) in accordance with "Average Brightness of IC Package" as disclosed in Japanese Laid Open Patent Application (JP-A-Heisei, 11-14317), instead of the equation (3):

$$thr = (\text{Average Brightness of IC Package}) \times (\text{Threshold Setting \%}) \quad (6)$$

Figure 5:
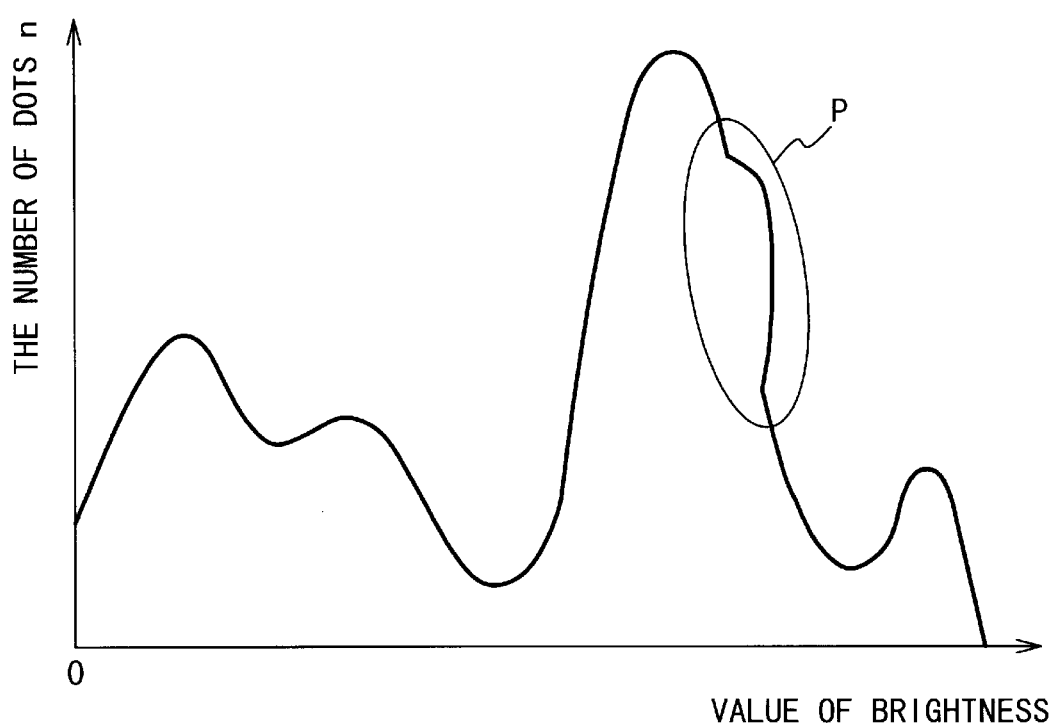
FIG. 5 is a view describing a problem when an average brightness is determined from the histogram of FIG. 2.

The calculation method based on the gazette "Average Brightness of IC Package" has the following problem. If there is a defect of a large white dirt in the IC package 8, a portion P corresponding to the defect of the white dirt exists on the histogram wave form, as shown in FIG. 5. According to the gazette, "Average Brightness of IC Package" includes the brightness of the portion P. Thus, there may be the fear that the thr is determined in accordance with the defective sample having the defect of the white dirt. So, according to the technique of the gazette, the thr is again calculated from "Average Brightness of IC Package", under the condition that the IC package judged as the allowed product is targeted, as the result of the binary conversion based on the determined thr. The second thr is used as the regular threshold level.

At the time of the determination of the threshold level, it is completed by only one operation, in this embodiment. Thus, the process speed is faster than that of the method noted in the gazette, which requires the two operations. This is because in the equation (3), since the threshold level is calculated in accordance with the peak value $n'_a$ of the histogram wave form, the brightness of the portion P of FIG. 5 does not have any influence on it.

However, there may be an inconvenient case when the threshold level is calculated in accordance with the peak value $n'_a$ of the histogram wave form, such as the equation (3).

If an inspection target region is wide such as the case when the IC package 8 is inspected as a whole, the defect such as the white dirt defect and the void has no influence on the peak value ($n'_a$) of the histogram wave form (the fact that the number of dots in the defect portion is maximum in the wide inspection target region can not be actually considered). Thus, even if the threshold level is calculated in accordance with the peak value $n'_a$ when the inspection target region is wide, the trouble is never induced.

On the contrary, in a case of a narrow inspection target region, an area rate of a defective portion is relatively larger than that of the case in the wide inspection target region, even if there is the defect of the same size. For this reason, when the histogram wave form corresponding to the narrow inspection target region is considered, it may be considered that the number of dots in the defective portion is maximum. In this case, let us suppose that the threshold level is calculated in accordance with the maximum number of dots, the threshold level is calculated in accordance with the defective (erroneous) portion. Thus, this disturbs the judgment of the allowance or rejection with regard to the desirable binary conversion.

The inspection of the narrow inspection target region is done in the condition that the portion of the IC package 8 is masked except the inspection target region.

In the case of the narrow inspection target region, a threshold level implying a fixed value (standard value) is used instead of the calculation method based on the equation (3), in order to remove the influence from the defective portion. If there is the photograph condition such as the illumination strength or the like is different, the fixed value is changed by the amount corresponding to the difference. As the changing method, the equation (7) is used as follows:

$$thrc = thrd \times (xs/xd) \quad (7)$$

however, the thrc is the changed threshold level, the thrd is the threshold level as the fixed value, the xs is the brightness corresponding to the peak value of the histogram wave form with regard to the entire IC package 8 targeted for the measurement, and the xd is the brightness as the fixed value corresponding to the peak value of the histogram wave form with regard to the entire IC package (a standard IC package when the fixed value thrd is determined).

Figure 6:
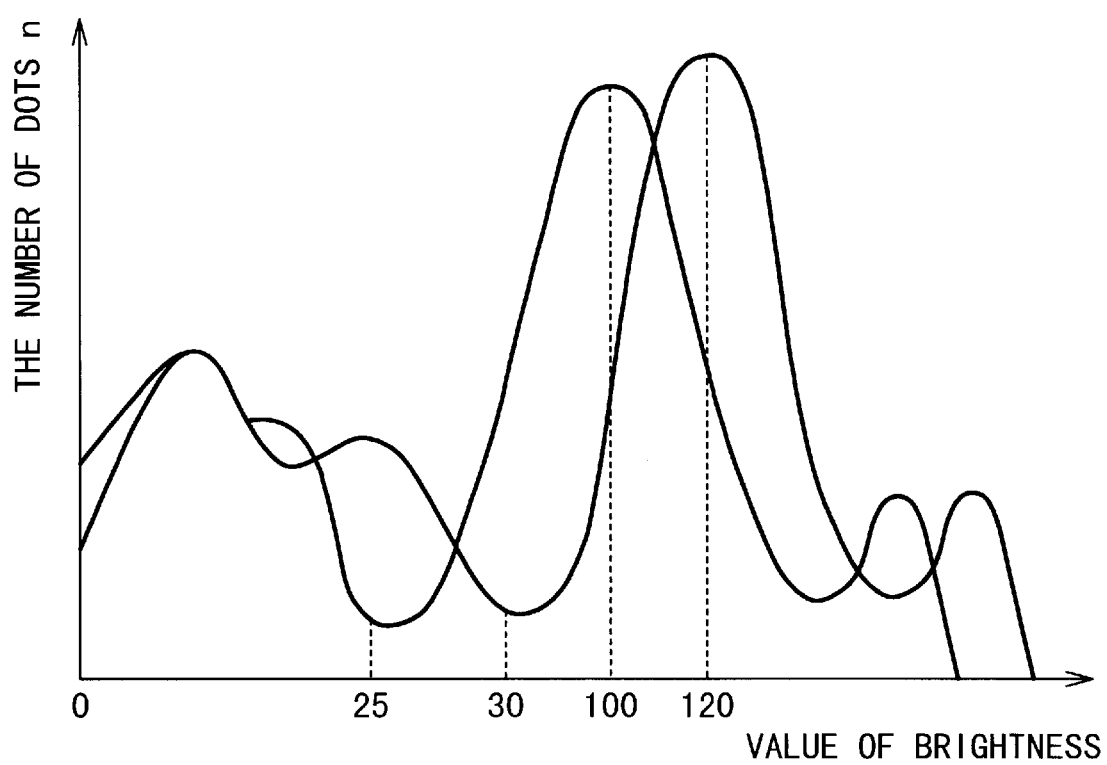
FIG. 6 is a view showing a histogram wave form when a photograph condition is different.

For example, as shown in FIG. 6, let us suppose that the brightness xd as the fixed value corresponding to the peak value of the histogram wave form with regard to the entire standard IC package is 120 and the threshold level thrd as the fixed value is 30. When the brightness xs corresponding to the peak value of the histogram wave form with regard to the entire IC package 8 targeted for the measurement is 100, the changed threshold level thrc is determined by the following equation (7)':

$$thrc = 30 \times (100/120) = 25 \quad (7')$$

Figure 7A:
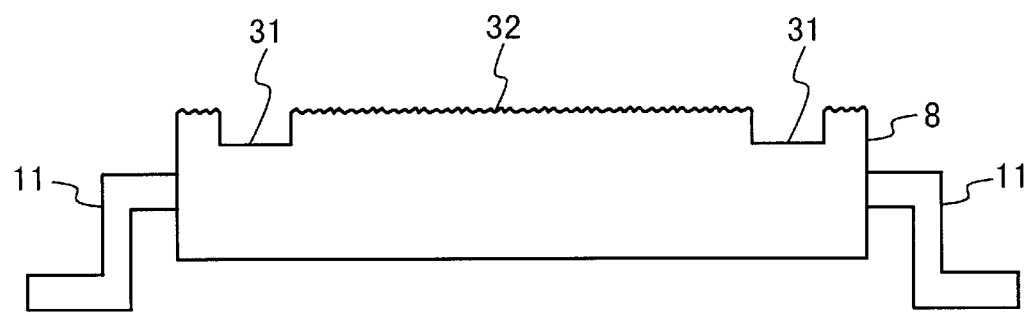
FIG. 7A is a side view showing an IC package.
Figure 7B:
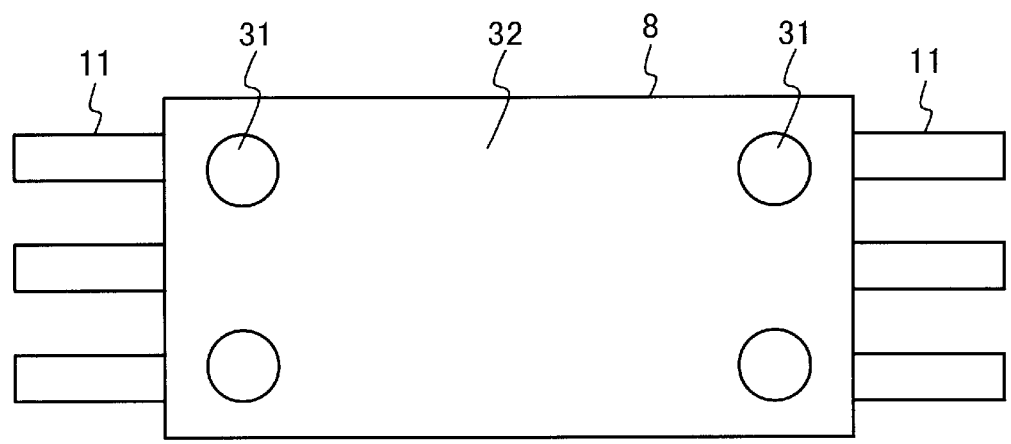
FIG. 7B is a plan view showing a top surface of the IC package.

The case of the narrow inspection target region includes a case in which a so-called pin mark is inspected. The pin mark is a pin push hole (concave) used when the IC package 8 is pushed out from a die by using a push pin (ejection pin) at a time of a mold. As shown in FIGS. 7A, 7B, one or four pin marks are formed at corners on the top surface 10 of the IC package 8.

A light reflection state is different between a pin mark region 31 and a region (resin body region) 32 besides the pin mark region 31 on the top surface 10 of the IC package 8. Typically, in the case that the pin mark is normally formed, the pin mark region 31 is inferior in brightness to the resin body region 32. For this reason, as mentioned above, if the pin mark region 31 is inspected, the judgment of the allowance or rejection with regard to the binary conversion is done in the condition that the resin body region 32 is masked. If the resin body region 32 is inspected, the judgment of the allowance or rejection with regard to the binary conversion is done in the condition that the pin mark region 31 is masked.

The case of the inspection of the resin body region 32 is firstly described.

Figure 8:
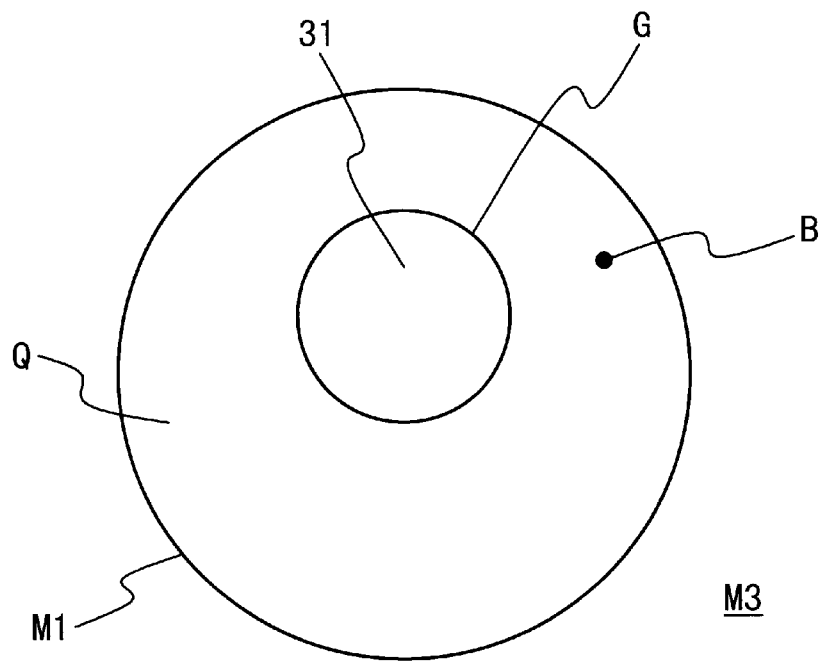
FIG. 8 is a view showing a mask to be fixedly used.

In this case, the pin mark region 31 is masked as mentioned above. Here, as for the position of the pin mark in the IC package 8, variation may be induced depending on a sample targeted for an actual measurement. For this reason, a mask M1 that is formed larger by a predetermined margin than an outer edge G (diameter) of the actual pin mark, as shown in FIG. 8, so that the pin mark can be surely masked even if the position is varied. This mask M1 is fixedly (as a standard) used irrespectively of the variation of the position of the actual pin mark.

The problem when the mask M1 is fixedly used is as follows.

The mask M1 in which the margin is reserved causes not only the actual pin mark region 31 but also a part Q of the resin body region 32 around the pin mark region 31 to be masked. Thus, it is not detected if a defect such as a void B exists in the masked resin body region Q.

Figure 9:
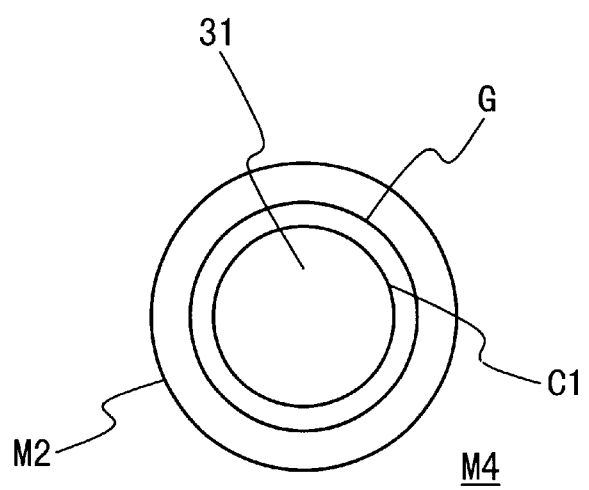
FIG. 9 is a view showing a mask based on a position of a pin mark.

Instead of the fixedly used mask M1, a mask M2 corresponding to the position of the pin mark may be used as shown in FIG. 9. The defect of the resin body region 32 around the pin mark region 31 can be detected by using the mask M2 in which the position of the actual pin mark is correctly reflected.

The mask M2 is formed as follows. As mentioned above, a pin mark detection window (not shown) is set for a region in which a pin mark is expected to be located. A pin mark model picture data registered in advance in the window is used to carry out a pattern matching. A position of the pin mark in the actual measurement target object is accurately detected by the pattern matching. The mask M2 is formed in which a diameter is extended by a preset predetermined value with respect to the outer edge G of the pin mark whose position is detected. The reason why the mask M2 whose diameter is extended by the predetermined value is that the outer edge (the portion of the stage with regard to the resin body region 32) G of the pin mark is not contained in the inspection region of the resin body region 32. At this time, if the region masked by the mask M2 is excessively larger than the actual pin mark region 31, the defect of the resin body region 32 around the pin mark region 31 is not detected as mentioned above.

Then, the case of the inspection of the pin mark region 31 is described.

In this case, the resin body region 32 is masked as mentioned above. As for the mask used at this time, a mask M3 in which an opening (a region corresponding to a symbol M1) larger by a set margin than the diameter (outer edge) of the pin mark is formed may be used, as shown in FIG. 8, so that the pin mark region 31 is surely exposed even if there is a variation in the pin mark position.

Or, a mask having an opening corresponding to a position of a pin mark may be used instead of the fixedly used mask M3. A mask M4 having an opening C1 whose diameter is reduced by a preset value with respect to the outer edge G of the pin mark whose position is correctly detected is formed as a result of the pattern matching, as shown in FIG. 9. The reason of the formation of the opening C1 whose diameter is reduced by the set value is that the outer edge (stage) G of the pin mark is not contained in the inspection region of the pin mark region 31 (pin mark inspection region).

The case of the inspection of the pin mark region 31 is further described.

At first, the pin mark is finely detected by the above-mentioned pattern matching. Then, the range in which the diameter is slightly reduced with respect to the pin mark is defined as the pin mark inspection region so as not to include the boundary line (stage) G of the detected pin mark.

As shown in FIG. 2, the histogram wave form is generated which targets all the dots of the photograph picture 1 in the IC package (in the data treatment range window 4) as a whole. The portion (wave form) indicative of the pin mark inspection region is extracted from the histogram wave form (FIG. 2), in accordance with the brightness and the dot number n (mountain).

Or, a data treatment window (not shown) is created in the pin mark inspection region. Then, the histogram wave form is generated which targets all the dots of the photograph picture 1 in the window.

Figure 10:
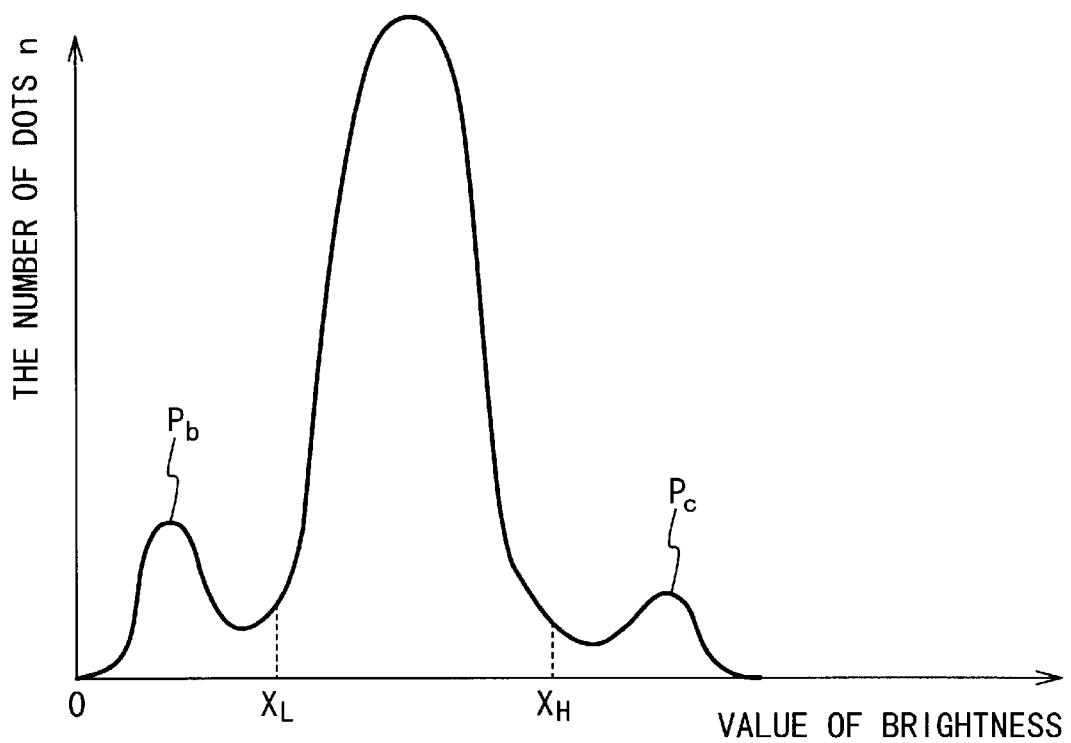
FIG. 10 is a view showing a histogram wave form in a pin mark inspection region.

FIG. 10 shows the wave form portion indicative of the pin mark inspection region extracted from the wave form of FIG. 2. Or, it may be considered that FIG. 10 shows the histogram wave form targeting the inside of the window created in the pin mark inspection region (and so forth; etc.).

A preset fixed value (standard value) is used as a threshold level when a pin mark inspection region is converted into a binary value. Or, the threshold level modified by the equation (7) may be used after an addition of a photograph condition.

If the inspection target region is narrow such as the pin mark inspection region, the area rate to the inspection target region of the defective portion becomes relatively higher as mentioned above. So, the value shown in the histogram wave form (FIG. 10) of the pin mark inspection region is noted to then select the threshold level. Thus, the judgment of the allowance or rejection with regard to the binary conversion is disturbed.

The two threshold levels of the fixed value (or, the values modified by the equation (7)) are used at the time of the inspection of the pin mark inspection region. The binary conversion process is performed a total of two times on the pin mark inspection region, in accordance with the respective two threshold levels.

The threshold level used at one of the threshold levels (hereafter, referred to as a first threshold level) is a brightness value $x_L$ lower than a brightness corresponding to the normal pin mark inspection region (having no defect) as shown in FIG. 10.

The threshold level used at the remaining one (hereafter, referred to as a second threshold level) is a brightness value $x_H$ higher than the brightness corresponding to the normal pin mark inspection region (having no defect).

When the pin mark inspection region is converted into a binary value in accordance with the first threshold level $x_L$, a portion indicated in black implies a void in the pin mark inspection region. In FIG. 10, a component Pb (a mass of a dot number) having a brightness value lower than the first threshold level $x_L$ indicates a void.

When the pin mark inspection region is converted into a binary value in accordance with the second threshold level $x_H$, a portion indicated in white implies an extraneous substance such as a white dirt in the pin mark inspection region, a shape error in the pin mark region, an edge of a void and the like. In FIG. 10, a component Pc (a mass of a dot number) having a brightness value higher than the second threshold level $x_H$ indicates the extraneous substance such as the white dirt, the shape error in the pin mark region, the edge of the void and the like.

When the mold product (IC package 8) is pushed from the die by the push pin, if there is a defect, such as a flaw, a loss and the like, at the tip of the push pin, the defect causes the concave and the convex to be induced in the pin mark. The illumination to the concave and the convex brings about an irregular reflection, which results in a brightness value higher than the second threshold level $x_H$. The shape error in the pin mark inspection region, the edge of the void and the like may be brought about by the defect at the tip of the push pin.

Differently from the resin body region 32, there is no seal in the pin mark region 31. Thus, the component having a brightness value higher than a certain value can be always judged as a defect, in the pin mark inspection region.

Figure 11A:
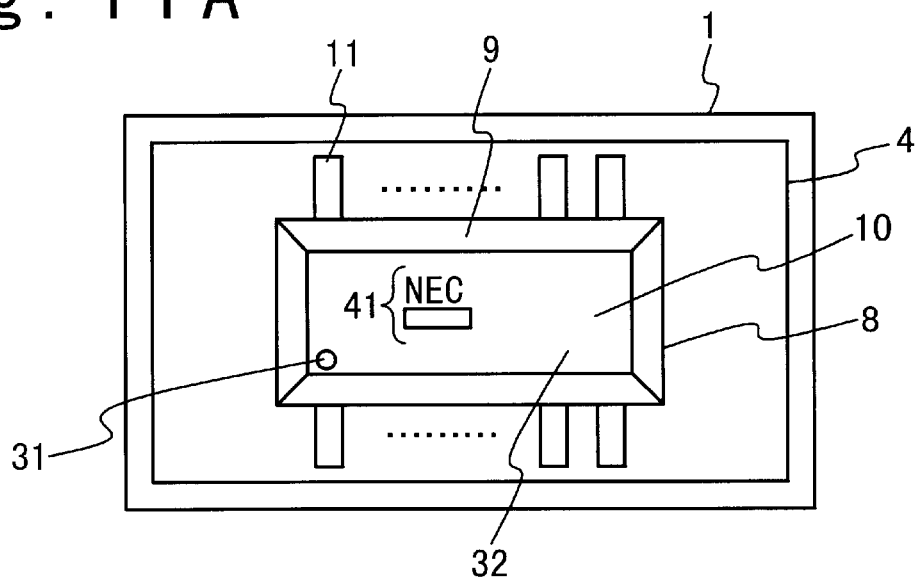
FIG. 11A is a plan view showing a data treatment range window with regard to an entire IC package, illustrating a seal of the IC package.
Figure 11B:
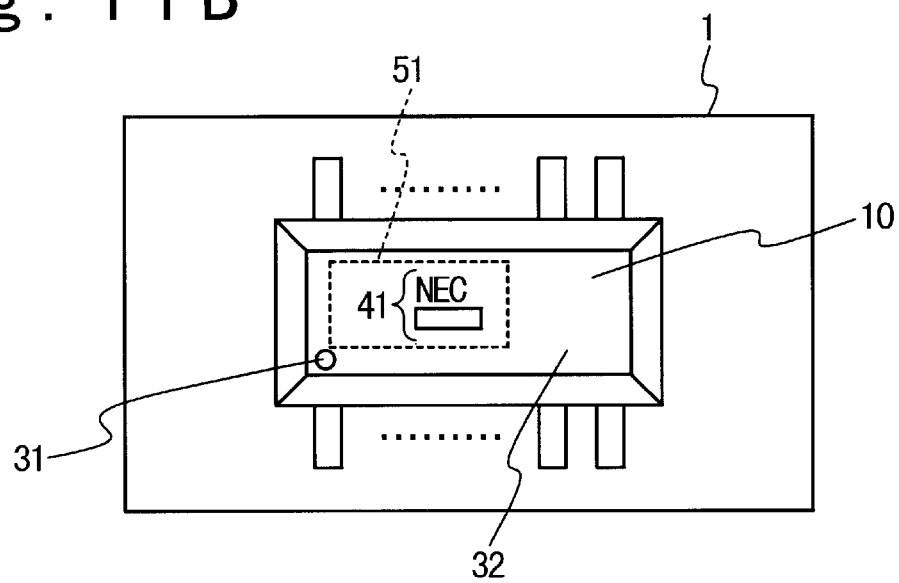
FIG. 11B is a view showing a data treatment range window with regard to a seal inspection region.

As shown in FIGS. 11A, 11B, the resin body region 32 contains a seal 41. So, the component having a brightness value higher than a certain value can not be always judged as a defect, in the resin body region 32 containing the seal 41. When the resin body region 32 from which the region of the seal 41 is removed is targeted, the component having the brightness value higher than the certain value can be firstly judged as the defect.

By the way, as mentioned above, when the histogram wave form is generated for the photograph screen 1 in the data treatment range window 4 (the entire IC package), its histogram wave form is generated in the condition that the pin mark region 31 is masked. If it is not so, the discrimination between the voids in the pin mark region 31 and the resin body region 32 is impossible as the similarly low brightness.

The case of the inspection of the seal will be described below.

When the seal 41 is inspected, it is necessary to identify the seal 41 in the entire region of the IC package 8, as the result of the binary conversion. The threshold level to convert into a binary value so as to identify the seal 41 is determined by using each of the following methods (a) to (c).

(a) It is possible to use the histogram wave form (FIG. 2) with regard to the entire IC package. A value for a seal inspection is prepared in advance as the multiplication value and/or the offset value in the equation (3). A threshold level thr for the seal inspection is calculated by using the equation (3) into which the value is substituted. The photograph screen 1 in the data treatment range window 4 (the entire IC package) is converted into a binary value, in accordance with the threshold level thr for the seal inspection. The seal 41 is detected as the component having the higher brightness than that of the thr after the binary conversion process.

According to this embodiment, once the histogram (FIG. 2) is generated with regard to the data treatment range window 4 (IC package 8), the histogram can be used for a plurality of inspection items only by changing the multiplication value and/or the offset value, as mentioned above. Thus, the process speed is very fast.

(b) As shown in FIG. 11b, a data treatment window (not shown) is generated in a seal inspection region 51 in which the seal 41 is expected to be contained. Accordingly, a histogram wave form (not shown) can be generated which targets the inside of the window. The method of generating the window is similar to the above-mentioned case. Also in this case, the threshold level thr is calculated by the equation (3). At that time, the value substituted into the equation (3) as the $n'_a$ is the smoothed peak value (corresponding to the brightness on the top surface 10 of the IC package 8) in the histogram targeting the seal inspection region 51. Also, the value substituted into the equation (3) as the multiplication value and/or the offset value is the value prepared in advance for the seal inspection.

A mountain (indicative of the dot number of the seal 41) having a higher brightness than the $n'_a$ corresponding to the brightness on the top surface 10 of the IC package 8 can be evidently detected from the histogram targeting the seal inspection region 51. This is because the component (the white dirt defect, the lead and the like) having a higher brightness which exists in a region besides the seal inspection region 51 does not appear in the histogram targeting the seal inspection region 51.

(c) The seal 41 can be extracted from the entire region of the IC package, in accordance with the histogram wave form (FIG. 2) with regard to the entire IC package. A plurality of methods will be described below with regard to the extracting method.

Figure 12:
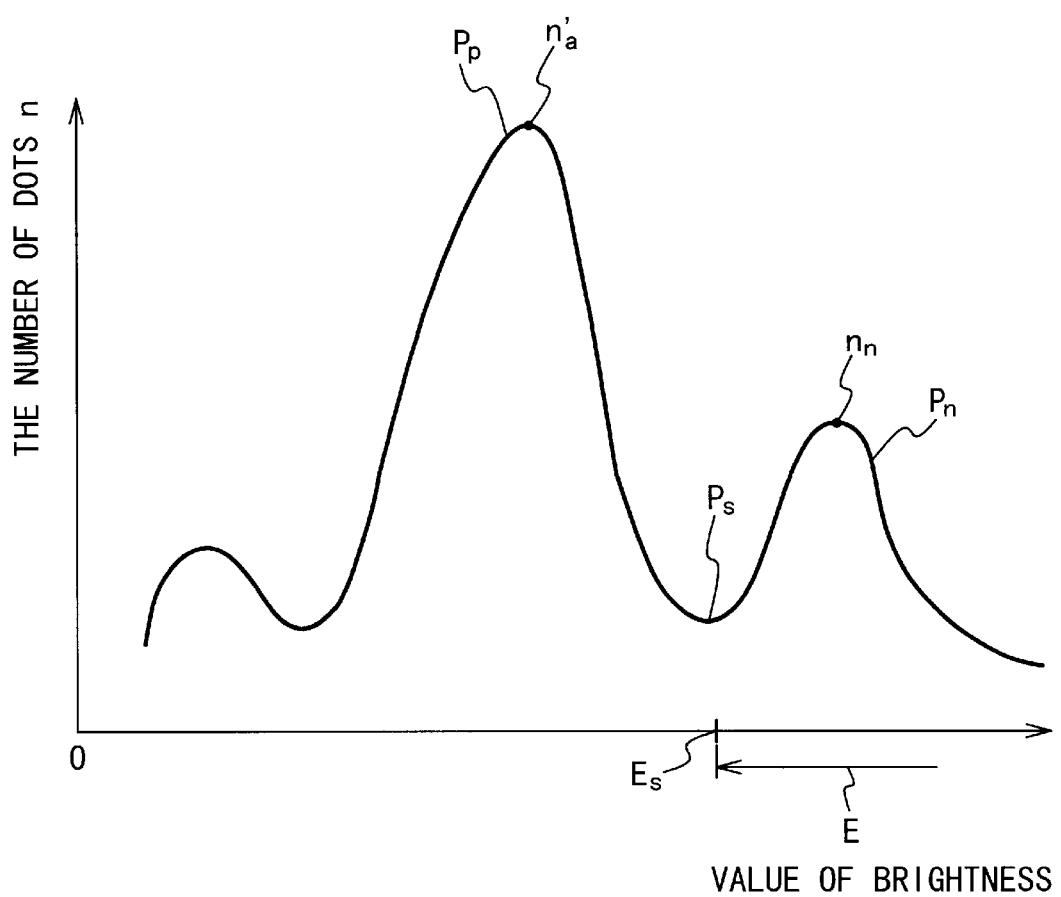
FIG. 12 is a view showing a histogram wave form with regard to an entire IC package and describing a method for extracting a seal from an entire region of the IC package.

FIG. 12 shows a histogram wave form targeting all dots of the photograph picture 1 in the data treatment range window 4, similarly to FIG. 2. Here, FIG. 12 shows the histogram when a seal is contained in a resin portion. In FIG. 12, a next peak in a brighter peak value corresponding to its resin region corresponds to the seal region. By the way, in a case of a histogram targeting all the dots in the data treatment range window 4, a peak in a lead region exists outside the further brighter portion of a peak corresponding to the seal region. However, the peak in the lead region is not shown in FIG. 12.

(c-1) A First Extracting Method is Firstly Described.

At first, the peak value $n'_a$ is determined which is smoothed in accordance with the equation (1) or (2). As shown in FIG. 12, with the $n'_a$ as a start point, the histogram wave form is scanned in a direction of a high brightness. A peak value $n_n$ of a mountain Pn next to a mountain Pp of the $n'_a$ is determined as the result of the scanning. The threshold level thr for the seal inspection is determined by the following equation (8):

$$thr=(n'_a+n_n)/2 \qquad (8)$$

The following equation (9) may be used instead of the equation (8):

$$Thr=(n'_a+n_n)/2\times \text{(Multiplication Value)}+\text{(Offset Value)} \qquad (9)$$

The multiplication value and/or the offset value in the equation (9) are used for the following object. The usage of the multiplication value and/or the offset value enables the calculation of a value lower than the thr determined in accordance with the equation (8), and the seal 41 can be clearly taken after the binary conversion. Or, a value higher than the thr determined in accordance with the equation (8) is not calculated so that a noise is not taken after the binary conversion.

(c-2) Next, a Second Extracting Method is Described.

Similarly to the first extracting method, the peak value $n'_a$ is firstly determined which is smoothed in accordance with the equation (1) or (2). With the $n'_a$ as the start point, the histogram wave form is scanned in the direction of the high brightness. A peak value $n_n$ of a mountain Pn next to a valley Ps of the mountain Pp of the $n'_a$ is determined as the result of the scanning. The $n_n$ determined by this second extracting method is substituted into the equation (8) or (9).

(c-3) Next, a Third Extracting Method is Described.

In the 256 gradations indicative of the entire region (the photograph picture 1 in the data treatment range window 4) of the IC package 8 implying the monochrome data, the brightness of the seal 41 is set in advance. A range E (refer to FIG. 12) of the set brightness is defined as a seal inspection range. The $n_n$ is determined as a peak of a histogram wave form in the seal inspection range E. The $n_n$ determined by the third extracting method is substituted into the equation (8) or (9).

(c-4) Next, a Fourth Extracting Method is Described.

The seal inspection range E is determined as follows. A lower limit value Es of the seal inspection range E is firstly determined by the following equation (10):

$$Es=n'_a\times\text{Set Multiplication Value}+\text{Set Offset Value} \qquad (10)$$

A range (having no upper limit) of a brightness higher than the Es determined by the equation (10) is defined as the seal inspection range E. The $n_n$ is determined as a peak of a histogram wave form in the seal inspection range E. The $n_n$ determined by the fourth extracting method is substituted into the equation (8) or (9).

The threshold level thr for the seal inspection is determined by any of the methods (a) to (c-4). The binary conversion is done in accordance with the thr. Thus, the seal 41 is extracted in the photograph picture 1, and the seal 41 is inspected.

In the seal inspection, the window can be generated in the seal inspection region 51, such as the above-mentioned item (b), to then generate the histogram wave form in the window. Also in the pin mark inspection region, similarly, the dedicated window can be generated to then generate the histogram wave form in the window. However, as shown in FIG. 7A, the surface conditions (roughness and the like) of the pin mark region 31 are different from those of the resin body region 32, and its brightness is evidently different. Thus, the portion of the wave form corresponding to only the pin mark region 31 can be easily extracted even from the histogram wave form (FIG. 2) with regard to the IC package as a whole. On the other hand, the seal inspection region 51 is mounted on a part of the resin region body 32, and there is no difference with regard to the surface condition and the like. Thus, it is difficult to discriminate the seal inspection region 51 from another resin region body 32, in the histogram wave form (FIG. 2) with regard to the entire IC package. From the viewpoint of the above points, the seal inspection region 51 has the relatively large merit with regard to the formation of the dedicated histogram wave form, while the pin mark region has the relatively small merit with regard to it.

An appearance inspection apparatus of a second embodiment will be described below with reference to FIGS. 13 to 16. The second embodiment is the appearance inspection apparatus for attaining the appearance inspection method of the first embodiment.

Figure 13:
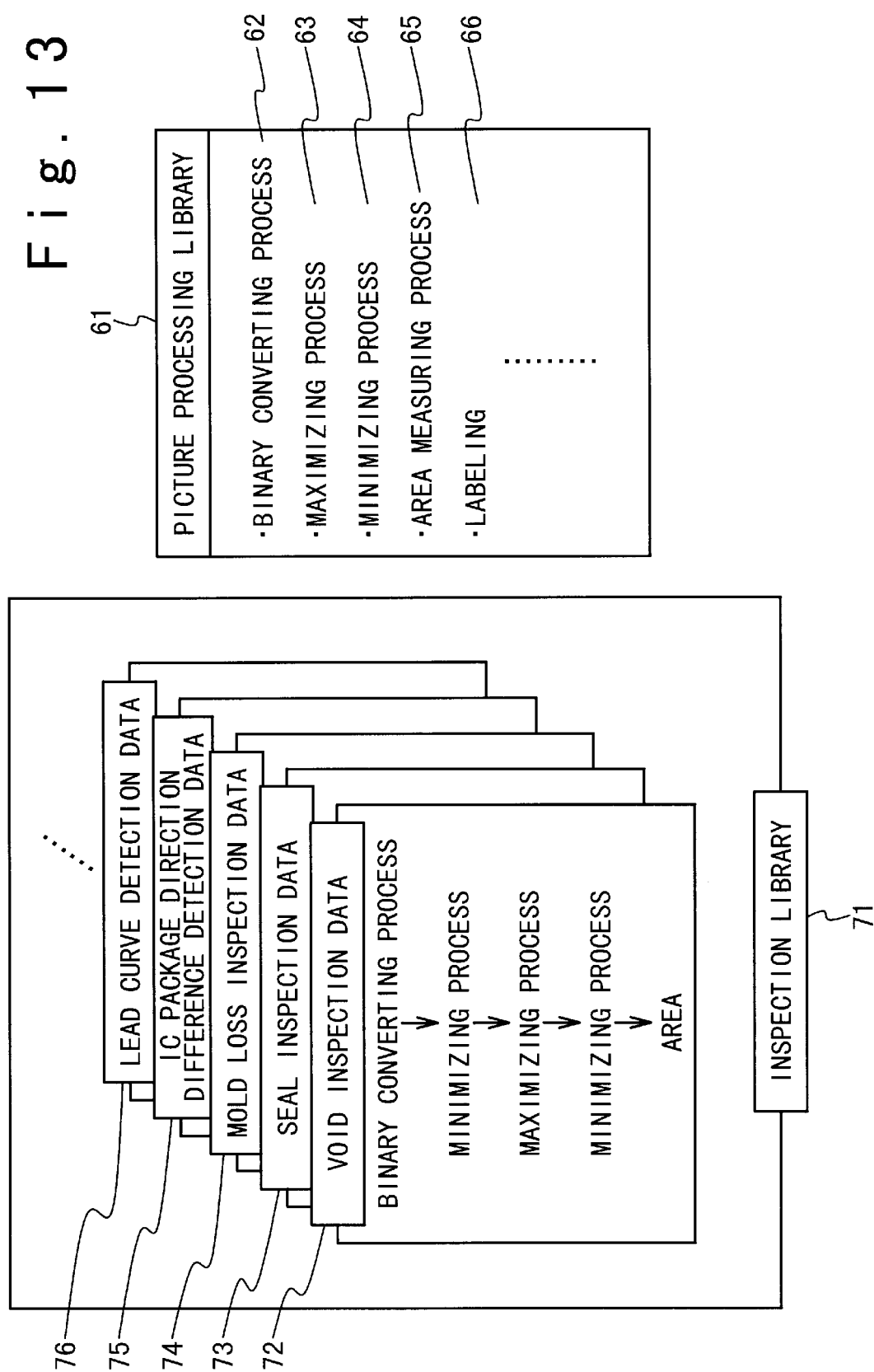
FIG. 13 is a view showing a picture processing library and an inspection library in a second embodiment of an appearance inspection apparatus according to the present invention.

As shown in FIG. 13, a plurality of basic picture processing items are stored in a picture processing library 61. Their picture processing items include a binary converting process 62, a maximizing process 63, a minimizing process 64, an area measuring process 65, a labeling 66 and the like. The binary converting process 62 includes the content of the first embodiment.

Here, the maximizing process 63 and the minimizing process 64 are described which are stored in the picture processing library 61. The maximizing process 63 and the minimizing process 64 are also referred to as an expanding process and a contracting process, respectively. Those processes are carried out in order to remove a noise (an isolated point) in the picture data.

Figure 14:
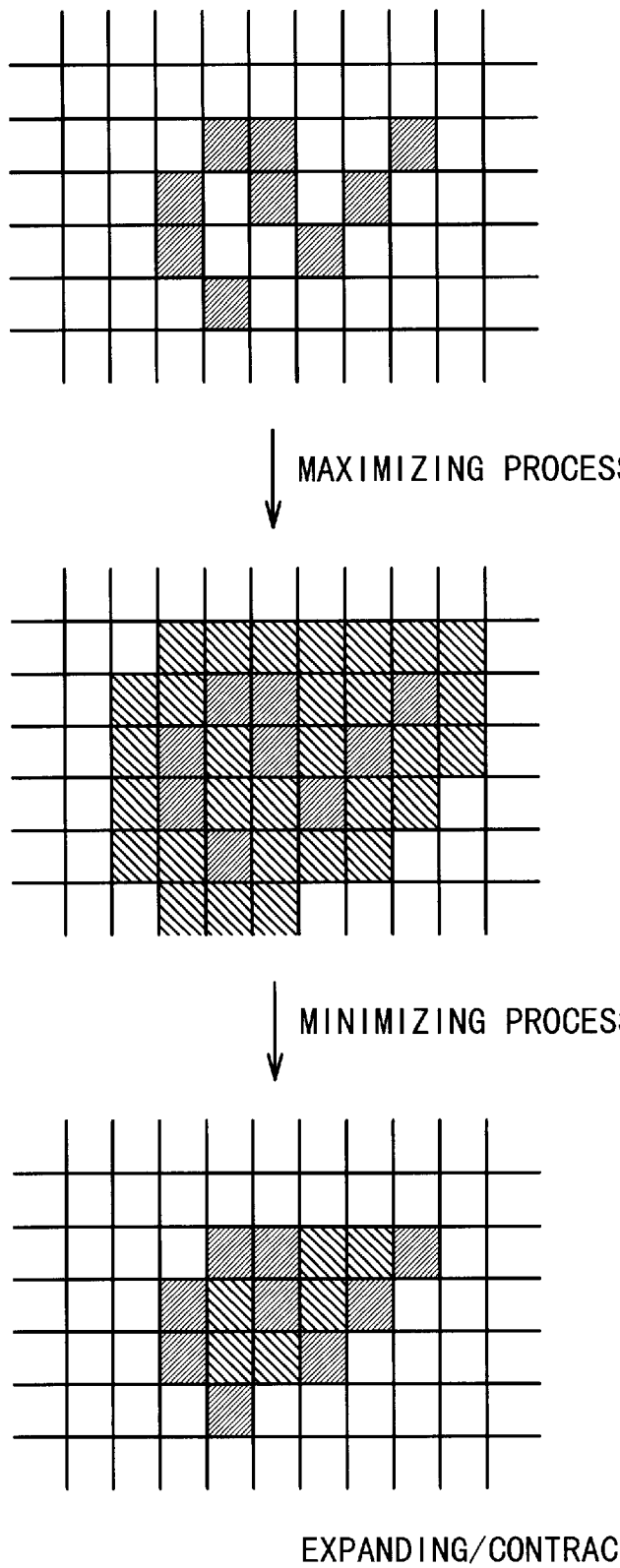
FIG. 14 is a view describing an expanding/contracting process.

As shown in FIG. 14, a periphery of a portion of a brightness [1] is firstly expanded, one by one. The expanding process is repeated for the set number of times. The periphery is contracted, one dot at a time. The contracting process is repeated for the set number of times. In this way, when a point of a fine brightness [0] is included in a dirty portion (periphery) indicative of the brightness [1] by the expanding/contracting process, the point of the brightness [0] can be converted into the brightness [1].

Figure 15:
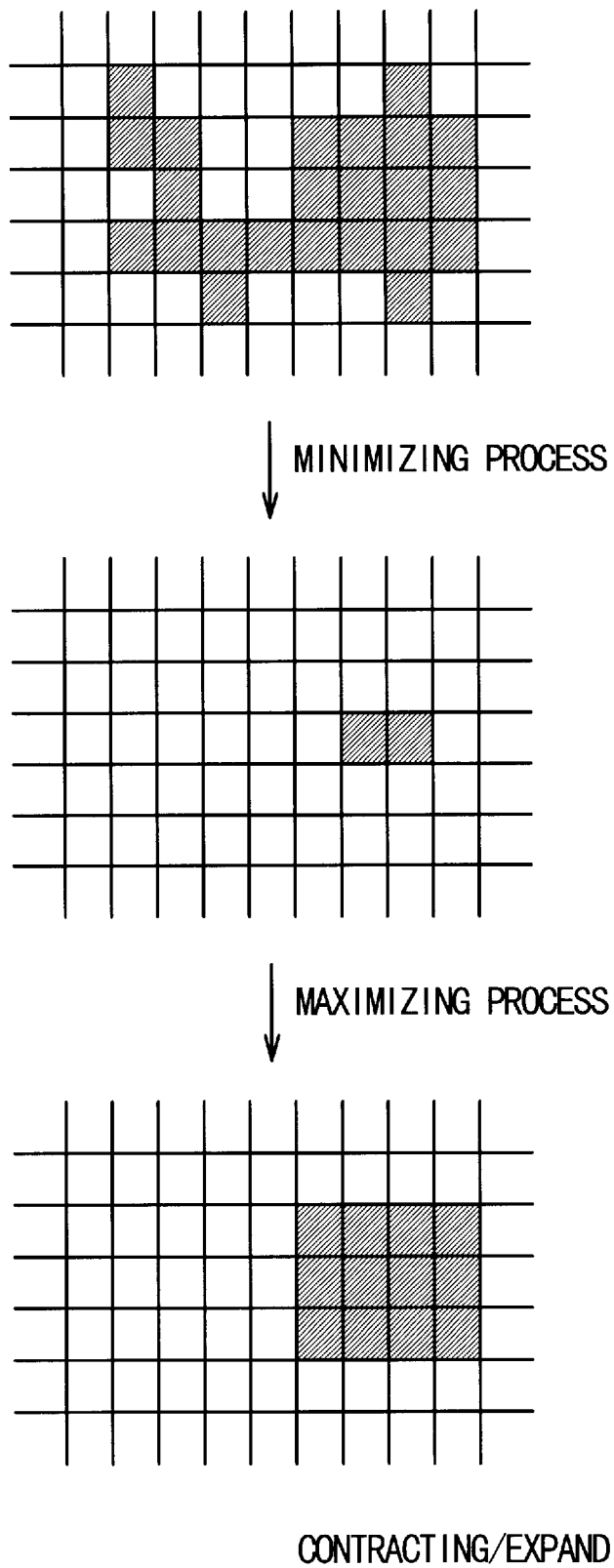
FIG. 15 is a view describing a contracting/expanding process.

On the contrary, the periphery of the portion having the brightness [1] is contracted, one dot at a time, as shown in FIG. 15. This contracting process is repeated for the set number of times. Then, the periphery is expanded, one dot at a time. This expanding process is repeated for the set number of times. In this way, when a point of a minute brightness [1] is included in a brightness [0] of an allowed product portion by the contracting/expanding process, the point of the brightness [1] can be converted into the brightness [0].

As mentioned above, the expanding/contracting process and the contracting/expanding process can remove the isolated points with regard to the regions of the brightnesses [1], [0]. The removal of the isolated points through those processes is experimentally confirmed.

The user refers to the picture processing library 61 and generates an inspection item data. The inspection item data includes a void inspection data 72, a seal inspection data 73, a mold loss inspection data 74, an IC package direction difference detection data 75, a lead curve detection data 76 and the like. The user, when generating the respective inspection item data 72 to 76, can arbitrarily select each of the picture processing items 62 to 66 stored in the picture processing library 61 and arbitrarily set an order of an execution of each selected picture processing item. The user can make the respective inspection item data 72 to 76 include parameters. For example, the user can make the inspection item data include the multiplication value and/or the offset value of the equation (3) for each inspection item (the detection of the void, the inspection of the seal or the like), the thrd and the xd in the equation (7), the dot number serving as the judgment standard with regard to the presence or absence of the seal, and the like. The names of the respective inspection items, such as the detection of the void, the inspection of the seal, the detection of the mold loss, the direction difference detection of the IC package, the detection of the lead curve and the like, are registered in the inspection item data 72 to 76.

Figure 16:
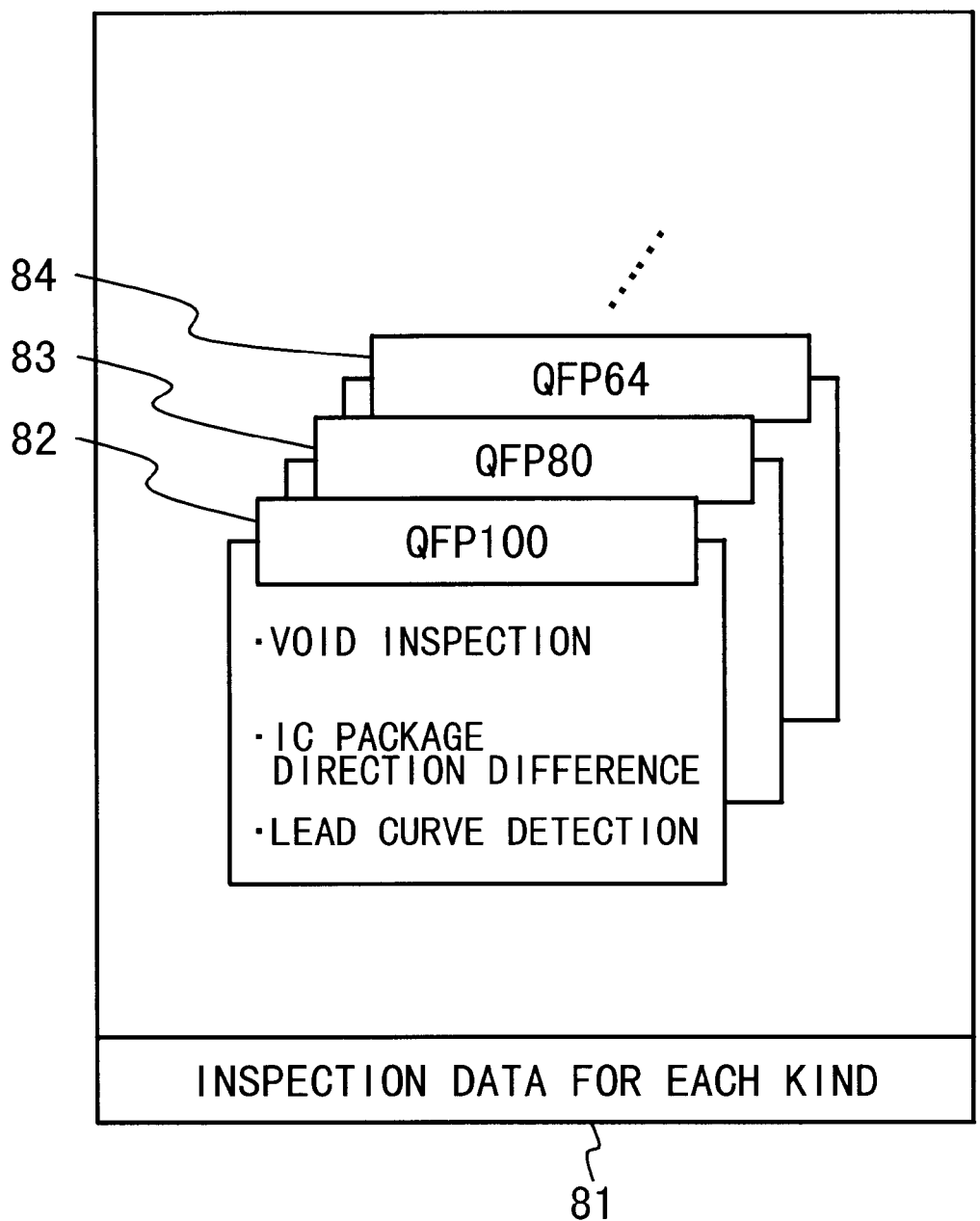
FIG. 16 is a view showing an inspection data for each kind.

The inspection item data 72 to 76 are stored in an inspection library 71. The user refers to the inspection library 71 and generates an inspection data for each kind 81. As shown in FIG. 16, the inspection data for each kind 81 is generated, for example, as a [QFP100] data 82, a [QFP80] data 83 and a [QFP64] data 84, for each inspection target product (type number). In the inspection target products [QFP100], [QFP80] and [QFP64], their inspection regions and their inspection items are different from each other. Thus, the user, when generating the inspection data for each data 82 to 84, can arbitrarily select each of the inspection item data 72 to 76 stored in the inspection library 71 and arbitrarily set an order of an execution of each selected inspection item data.

The user, when generating the respective inspection data for each kind 82 to 84, does not generate them by referring to the picture processing library 61 and combining the respective picture processing items 62 to 66. So, the user generates the respective inspection data for each kind 82 to 84 by referring to the inspection library 71 and combining the respective inspection item data 72 to 76. Thus, the user can easily generate the respective inspection data for each kind 82 to 84.

In this embodiment, picture processing algorithms 72 to 76 (the inspection library 71) are generated in which the various algorithms 62 to 66 for the picture process stored in advance as the picture processing library 61 are combined and duplicated in any order by the user. The user gives any name to the duplicated picture processing algorithms 72 to 76 and stores in the inspection library 71.

The user specifies the uniquely generated picture processing algorithms 72 to 76 within the inspection data 81 for each kind, by using the name at the time of the registration. Accordingly, the picture processing algorithms 72 to 76 are commonly used even at the time of the generation of the inspection data 82 to 84 of the different kinds. Moreover, the picture processing algorithms 72 to 76 are individually changed within the inspection data 82 to 84 for each kind.

The picture processing algorithms 72 to 76, the inspection region and the judgment value are set for the inspection data for each kind 82 to 84. At a time of an automatic inspection, the picture process is done in the specified inspection region, in accordance with the preset inspection data 72 to 76. The allowance or rejection is judged by the comparison between the finally measured value and the judgment value.

The inspection result is outputted to any address for each inspection item arbitrarily generated by the user.

In the above-mentioned explanations, the case in which except the case of the usage of the standard value, the threshold level is determined in accordance with the histogram wave form, and the defect is detected by the binary conversion process in accordance with the threshold level. The first and second embodiments are not limited to the above-mentioned method using the histogram. They can be also applied to the calculation of the threshold level used in the projection methods (Japanese Laid Open Patent Application (JP-A-Heisei, 7-128249), Japanese Laid Open Patent Application (JP-A-Heisei, 7-229842) and Japanese Laid Open Patent Application (JP-A-Heisei, 8-14845)).

According to the appearance inspection method of the present invention, the inspection processing speed is further fast.

According to another appearance inspection apparatus of the present invention, the user can generate the picture processing algorithm in any order.

What is claimed is:

1. An appearance inspection method, comprising:
   (a) providing an image data in which an inspected sample is photographed;
   (b) detecting a brightness of each of a plurality of image units included in said image data based on said image data;
   (c) detecting the number of said image units being identical with each other in said brightness for each of said brightness;
   (d) detecting, as a measured maximum number, the number that is maximum of the detected numbers as a result of said (c);
   (e) computing said measured maximum number to determine a set maximum number;
   (f) determining a threshold level of said brightness based on said set maximum number;
   (g) converting said image data into a binary pattern based on said threshold level; and
   (h) detecting a defect of said inspected sample based on said binary pattern.

2. An appearance inspection method according to claim 1, wherein said set maximum number corresponds to a result when a noise component is removed from said measured maximum number.

3. An appearance inspection method according to claim 1, wherein said (e) is performed with first and second numbers, said first number corresponding to higher brightness with reference to said brightness corresponding to said measured maximum number, and said second number corresponding to lower brightness with reference to said brightness corresponding to said measured maximum number.

4. The appearance inspection method according to claim 1, wherein said (e) is performed with said brightness corresponding to the number identical with a subtracted value after subtracting a predetermined value from said measured maximum number.

5. The appearance inspection method according to claim 1, wherein a result of said (b) is represented by a histogram, and
   wherein in said (e), a portion in which the number is larger than a subtracted value after subtracting a predetermined value from said measured maximum number of a waveform of said histogram, is approximated to a quadratic curve, and
   wherein a peak value of said quadratic curve is detected as said set maximum number.

6. The appearance inspection method according to claim 1, wherein thr=said set maximum number×a multiplication value+an offset value, and wherein thr is said threshold level of said (f).

7. The appearance inspection method according to claim 6, wherein at least one of said multiplication value and said offset value is different for each of a plurality of inspection items with regard to said inspected sample.

8. The appearance inspection method according to claim 7, wherein said inspected sample is an IC package, and said plurality of inspection items include a void inspection, a detection of a package crack and a package defect, a seal inspection, an extraneous substance on a lead inspection, and an extraneous substance between leads inspection.

9. The appearance inspection method according to claim 1, wherein when an inspecting target area to detect said defect is smaller than a preset value, said threshold level is not determined at said (d), (e) and (f), and a predetermined standard value is used as said threshold level.

10. The appearance inspection method according to claim 1, wherein said inspected sample is an IC package, a concave section is formed in said IC package, said concave section being provided for a pin to push said IC package out of a mold making industry when said IC package is molded, and
    wherein when an inspecting target area to detect said defect is said concave section, said threshold level is not determined at said (d), (e) and (f), and two predetermined standard values are used as said threshold level, and
    wherein said converting of said (g) is performed two time by using said two predetermined standard values as said threshold level, respectively to produce two said binary patterns, and
    wherein said (h) includes detecting different kind of said defect with each other based on each of said two binary patterns, respectively.

11. The appearance inspection method according to claim 1, wherein said inspected sample is an IC package, and said IC package includes a seal, and wherein when an inspecting target area to detect said defect is said seal, said (b) includes detecting said brightness of a seal inspection portion in which said seal is expected to exist of said image data, and
    wherein said (c) includes detecting the number of said image units with regard to said seal inspection portion.

12. The appearance inspection method according to claim 1, wherein said inspected sample is an IC package, and said IC package includes a seal, and
    wherein a result of said (b) is represented by a histogram, and
    wherein when an inspecting target area to detect said defect is said seal, said (f) includes scanning a waveform of said histogram from said set maximum number as a beginning point in direction to higher brightness, and
    wherein said (f) includes detecting a peak value of a first upward convex curve next to a second upward convex curve including said set maximum number of said waveform as a result of said scanning, and
    wherein thr=(said set maximum number+said peak value)/2, and wherein thr is said threshold level of said (f).

13. The appearance inspection method according to claim 1, wherein said inspected sample is an IC package, and said IC package includes a seal, and
    wherein a result of said (b) is represented by a histogram, and
    wherein when an inspecting target area to detect said defect is said seal, said (f) includes scanning a waveform of said histogram from said set maximum number as a beginning point in direction to higher brightness, and
    wherein said (f) includes detecting a peak value of a first upward convex curve next to a downward concave portion of a second upward convex curve including said set maximum number of said waveform as a result of said scanning, and wherein thr=(said set maximum number+said peak value)/2, and wherein thr is said threshold level of said (f).

14. The appearance inspection method according to claim 1, wherein said inspected sample is an IC package, and said IC package includes a seal, and wherein a result of said (b) is represented by a histogram, and wherein when an inspecting target area to detect said defect is said seal, said (f) includes setting a range corresponding to a predetermined brightness of said histogram as a seal inspection portion, and wherein a peak value in said seal inspection portion of a waveform of said histogram is detected, and wherein thr=(said set maximum number+said peak value)/2, and wherein thr is said threshold level of said (f).

15. The appearance inspection method according to claim 1, wherein said inspected sample is an IC package, and said IC package includes a seal, and wherein a result of said (b) is represented by a histogram, and wherein when an inspecting target area to detect said defect is said seal, said (f) includes setting a range in which Es is the lowest point in said brightness of said histogram as a seal inspection portion, and wherein said Es=said set maximum number×a set multiplication value+a set offset value, and wherein a peak value in said seal inspection portion of a waveform of said histogram is detected, and wherein thr=(said set maximum number+said peak value)/2, and wherein thr is said threshold level of said (f).

16. An appearance inspection apparatus, comprising:

a camera photographing an inspected sample to produce an image data of said inspected sample;

a threshold level providing section providing a threshold level;

a binary converting section converting said image data into a binary pattern based on said threshold level; and a judging section judging whether said inspected sample is passed or failed based on said binary pattern, and wherein said threshold level providing section detects a brightness of each of a plurality of image units included in said image data based on said image data, and detects the number of said image units being identical with each other in said brightness for each of said brightness, and detects, as a measured maximum number, the number that is maximum of the detected numbers, and computes said measured maximum number to determine a set maximum number, and provides said threshold level based on said set maximum number.

17. An appearance inspection apparatus, comprising:

an image processing library storing a plurality of image processing items;

an inspection library storing a plurality of inspection item data, in which said plurality of image processing items are selected arbitrarily and in which said selected image processing items are performed in an arbitrary turn, and wherein a binary converting process is included in said plurality of image processing items, and wherein said binary converting process includes detecting a brightness of each of a plurality of image units included in an image data in which an inspected sample is photographed based on said image data, when providing a threshold level used in said binary converting process, and detecting the number of said image units being identical with each other in said brightness for each of said brightness, and detecting, as a measured maximum number, the number that is maximum of the detected numbers, and computing said measured maximum number to determine a set maximum number, and providing said threshold level based on said set maximum number.

18. The appearance inspection apparatus according to claim 17, further comprising:

an inspection data for each kind library storing a plurality of inspection data for each kind for an inspection target product, in which said plurality of inspection item data are selected arbitrarily in which said selected inspection item data are performed in an arbitrary turn.

19. The appearance inspection apparatus according to claim 17, wherein a plurality of said inspection item data includes data for a void inspection, data for a seal inspection, data for a mold loss inspection, data for an IC package direction difference detection and data for a lead curve detection.

20. The appearance inspection apparatus according to claim 17, wherein a plurality of said inspection item data includes a parameter used in the computation included in said binary converting process.

21. A computer readable recording medium for recording a program for a process, comprising:

(a) providing an image data in which an inspected sample is photographed;

(b) detecting a brightness of each of a plurality of image units included in said image data based on said image data;

(c) detecting the number of said image units being identical with each other in said brightness for each of said brightness;

(d) detecting, as a measured maximum number, the number that is maximum of the detected numbers as a result of said (c);

(e) computing said measured maximum number to determine a set maximum number;

(f) determining a threshold level of said brightness based on said set maximum number;

(g) converting said image data into a binary pattern based on said threshold level; and (h) detecting a defect of said inspected sample based on said binary pattern.

* * * * *

UNITED STATES PATENT AND TRADEMARK OFFICE
CERTIFICATE OF CORRECTION

PATENT NO.   : 6,741,734 B2
DATED        : May 25, 2004
INVENTOR(S)  : Yoshihiro Sasaki and Masahiko Nagao It is certified that error appears in the above-identified patent and that said Letters Patent is hereby corrected as shown below:

<u>Column 2,</u>
Line 32, "Heisel" has been replaced with -- Heisei --.

Signed and Sealed this

Fifth Day of October, 2004

JON W. DUDAS
*Director of the United States Patent and Trademark Office*